US011331001B2

(12) United States Patent
Jacobsen et al.

(10) Patent No.: US 11,331,001 B2
(45) Date of Patent: May 17, 2022

(54) NAVIGATION FIELD DISTORTION DETECTION

(71) Applicant: Medtronic Navigation, Inc., Louisville, CO (US)

(72) Inventors: Brad Jacobsen, Erie, CO (US); Andrew Bzostek, Boulder, CO (US); Steven L. Hartmann, Superior, CO (US)

(73) Assignee: Medtronic Navigation, Inc., Louisville, CO (US)

( * ) Notice: Subject to any disclaimer, the term of this patent is extended or adjusted under 35 U.S.C. 154(b) by 1098 days.

(21) Appl. No.: 15/664,778

(22) Filed: Jul. 31, 2017

(65) Prior Publication Data

US 2017/0340240 A1    Nov. 30, 2017

Related U.S. Application Data

(63) Continuation of application No. 13/834,553, filed on Mar. 15, 2013, now Pat. No. 9,717,442.

(51) Int. Cl.
| | | |
|---|---|---|
| *A61B 5/06* | (2006.01) | |
| *G01S 5/02* | (2010.01) | |
| *G01S 7/02* | (2006.01) | |
| *G01S 7/40* | (2006.01) | |
| *A61B 34/20* | (2016.01) | |

(52) U.S. Cl.
CPC .............. *A61B 5/061* (2013.01); *A61B 34/20* (2016.02); *G01S 5/02* (2013.01); *G01S 7/023* (2013.01); *G01S 7/40* (2013.01); *A61B 2034/2051* (2016.02); *A61B 2034/2072* (2016.02)

(58) Field of Classification Search
CPC .... A61B 2034/2051; A61B 2034/2072; A61B 5/061; A61B 34/20
USPC ........................................................ 600/424
See application file for complete search history.

(56) References Cited

U.S. PATENT DOCUMENTS

| | | | |
|---|---|---|---|
| 5,592,939 | A | 1/1997 | Martinelli |
| 5,740,808 | A | 4/1998 | Panescu et al. |
| 5,840,024 | A | 11/1998 | Taniguchi et al. |
| 5,913,820 | A | 6/1999 | Bladen et al. |
| 6,230,042 | B1 | 5/2001 | Slettenmark |
| 6,266,552 | B1 | 7/2001 | Slettenmark |
| 6,381,485 | B1 | 4/2002 | Hunter et al. |

(Continued)

FOREIGN PATENT DOCUMENTS

| | | |
|---|---|---|
| DE | 102009021705 A1 | 11/2010 |
| EP | 2186474 A1 | 5/2010 |

OTHER PUBLICATIONS

Approximation of Minimum Energy Curves, R. Qu and J. Ye, Applied Math. and Comp, vol. 108, pp. 153-166, 2000.

(Continued)

*Primary Examiner* — James M Kish
(74) *Attorney, Agent, or Firm* — Harness, Dickey & Pierce, P.L.C.

(57) ABSTRACT

Disclosed is a method and system for navigating an instrument relative to a patient that can be near a field distorting feature. A localizer can generate an electromagnetic field that is sensed by a tracking device to determine a location of the tracking device with the sensed electromagnetic field. The system and related method can assist in determining whether a navigation field is distorted near a tracking device of the instrument.

25 Claims, 7 Drawing Sheets

(56) References Cited

U.S. PATENT DOCUMENTS

| | | |
|---|---|---|
| 6,474,341 B1 | 11/2002 | Hunter et al. |
| 6,636,757 B1 | 10/2003 | Jascob et al. |
| 6,892,090 B2 | 5/2005 | Verard et al. |
| 6,973,339 B2 | 12/2005 | Govari |
| 7,321,228 B2 | 1/2008 | Govari |
| 7,688,064 B2 | 3/2010 | Shalgi et al. |
| 7,706,859 B2 | 4/2010 | Aizawa et al. |
| 7,792,342 B2 | 9/2010 | Barbu et al. |
| 8,082,020 B2 | 12/2011 | Bar-Tal et al. |
| 8,260,400 B2 | 9/2012 | Govari et al. |
| 8,290,572 B2 | 10/2012 | Martinelli et al. |
| 9,717,442 B2 | 8/2017 | Jacobsen et al. |
| 2004/0215071 A1 | 10/2004 | Frank et al. |
| 2005/0024043 A1 | 2/2005 | Govari |
| 2005/0033135 A1 | 2/2005 | Govari |
| 2005/0085720 A1 | 4/2005 | Jascob et al. |
| 2005/0107687 A1 | 5/2005 | Anderson |
| 2006/0058647 A1 | 3/2006 | Strommer et al. |
| 2006/0173289 A1* | 8/2006 | Aizawa .......... A61B 5/064 600/424 |
| 2007/0270692 A1 | 11/2007 | Barbu et al. |
| 2008/0012553 A1 | 1/2008 | Shalgi et al. |
| 2008/0033282 A1 | 2/2008 | Bar-Tal et al. |
| 2008/0119727 A1 | 5/2008 | Barbagli et al. |
| 2008/0125646 A1 | 5/2008 | Govari et al. |
| 2008/0294034 A1 | 11/2008 | Krueger et al. |
| 2009/0082665 A1 | 3/2009 | Anderson |
| 2010/0160771 A1 | 6/2010 | Gielen et al. |
| 2011/0160570 A1 | 6/2011 | Kariv et al. |
| 2011/0160571 A1* | 6/2011 | Cohen .......... A61B 5/066 600/424 |
| 2011/0251814 A1 | 10/2011 | Bar-Tal et al. |
| 2011/0251815 A1 | 10/2011 | Bar-Tal et al. |
| 2012/0149966 A1 | 6/2012 | Ludwin et al. |
| 2012/0149967 A1* | 6/2012 | Ludwin .......... A61B 5/06 600/11 |

OTHER PUBLICATIONS

Constraint-Based LN Curves, Y. J. Ahn and C.M. Hoffmann, Computer Aided Geometric Design, vol. 29 pp. 30-40, 2012.

Curves and Surfaces for CAGD, A Practical Guide, 5th ed., G. Farin, Morgan-Kaufmann, Burlington, 2002. (28 pages).

Efficient Approximation of Minimum Energy Curves with Interpolatory Constraints, R. u and J. Ye, Applied Math. and Comp., vol. 109, pp. 151-166, 2000.

Energy Formulations of Algebraic Splines, C.L. Bajaj, et al. Computer Aided Geometric Design, vol. 16 pp. 39-59, 1999.

International Preliminary Report on Patentability and Written Opinion dated Sep. 24, 2015 for PCT/US2014/028005 claiming benefit of U.S. Appl. No. 13/834,553, filed Mar. 15, 2013.

International Search Report and Written Opinion dated Aug. 25, 2014 for PCT/US2014/028005 claiming benefit of U.S. Appl. No. 13/834,553, filed Mar. 15, 2013.

Methods of Mathematical Physics, vol. I., R. Courant and D. Hilbert, Interscience, New York, 1953, pp. 164-274.

Numerical Method for extracting an Arc Length Parameterization from Parametric Curves, R.J. Sharpe and R.W. Thorne, Computer-Aided Design, vol. 14 pp. 79-81, 1982.

Path Planning for Minimal Energy Curves of Constant Lenght, M. Moll and L.E. Kavraki, Proc. of the IEEE Int. Conf. on Rob. Auto., pp. 2826-2831, 2004.

The Curve of Least Energy, B.K.P Horn, ACM Trans. Math. SW, vol. 9 pp. 441-460, 1983.

The Length of Bezier Curves, J Gravesen, Graphics Gems V, p. 199-205, Academic Press Boston, 1995.

Williams, D.J., et al., "A Fast Algorithm for Active Countours and Curvature Estimation," CVGIP: Image Understanding, vol. 55, pp. 14-26 1992.

European Office Action dated Feb. 20, 2018 in corresponding European Application No. 14726027.7.

Extended European Search Report regarding EP 21175453.6, dated Aug. 10, 2021.

* cited by examiner

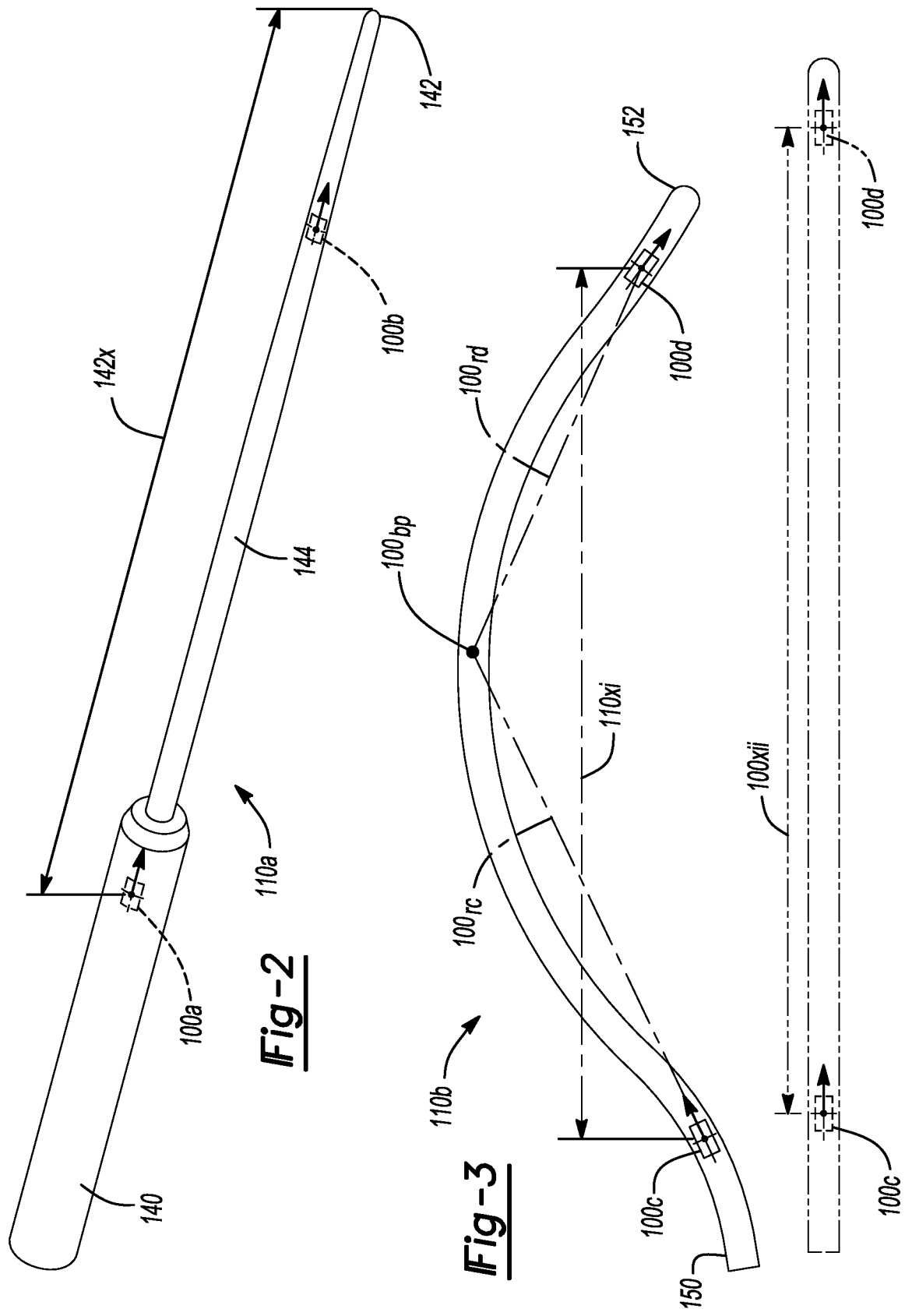

NAVIGATION FIELD DISTORTION DETECTION

CROSS-REFERENCE TO RELATED APPLICATIONS

This application is a continuation of U.S. patent application Ser. No. 13/834,553 filed on Mar. 15, 2013. The entire disclosure of the above application is incorporated herein by reference.

FIELD

The subject disclosure is related generally to a navigated procedure on a subject and particularly to determining possible or real distortion of an electromagnetic field.

BACKGROUND

This section provides background information related to the present disclosure which is not necessarily prior art.

In performing a procedure, a user, such as a surgeon, can perform a procedure on a subject with a navigation system. The navigation system can assist in determining a location of a tracked device, such as a scalpel, catheter, or deep brain stimulation probe, by tracking a tracking device associated with the tracked device. The tracked device can include the instruments noted above, to which a tracking device is associated, such as directly affixed thereto. The instrument can allow a procedure to be performed on a subject while illustrating the location of the instrument relative to the subject. The position of the instrument can be illustrated relative to the subject by superimposing an icon representing the instrument on an image of the subject.

Image data is often acquired of the subject for display prior to, during, and after a procedure on the subject. The image, including the image data which generates or is used to render the image, can be registered to the subject. The image data can define an image space that can include a three-dimensional space. The subject can likewise define a three-dimensional physical space to which the image data is registered. Registration can be performed in a plurality of processes.

According to various embodiments, a navigation system can use an electromagnetic navigation system (EM navigation system) to acquire or determine navigation information, including tracked locations of various tracking devices and relative locations to registered image data. In an EM navigation system, an electromagnetic field (EM field) is generated by a localizer and sensed by a tracking device. The localizer can be positioned relative to the subject space and a tracking device can be associated or positioned on the instrument, or vice versa. According to various embodiments, a localizer can be positioned on the instrument that can generate the EM field to be sensed by a tracking device positioned away from the instrument. It is understood that the EM field can be affected by conducting materials, such as metals or other conducting materials (e.g., conducting polymers or impregnated polymeric materials or devices), and magnetic materials (e.g. soft ferromagnetic iron).

SUMMARY

This section provides a general summary of the disclosure, and is not a comprehensive disclosure of its full scope or all of its features.

A navigation system can navigate an instrument with an electromagnetic (EM) field. The EM field can define a navigation space, such as within a subject, including a human patient. The EM field, however, can be distorted by distorting elements or features within the navigation space, such as conducting metals or materials and/or magnetic materials. When distortion of the field occurs then a location of the tracking device associated with an instrument may not be properly determined. The determination of the distorted field, however, may not be immediately determinable by user simply by viewing a navigated area. For example, if an instrument is placed within a patient, the location of the instrument may not be viewable by a user, but is rather being tracked by the tracking system. Accordingly, a determination of a distorted field assists in identifying and informing the user that a navigation should be altered, recalibrated or stopped.

Further areas of applicability will become apparent from the description provided herein. The description and specific examples in this summary are intended for purposes of illustration only and are not intended to limit the scope of the present disclosure.

DRAWINGS

The drawings described herein are for illustrative purposes only of selected embodiments and not all possible implementations, and are not intended to limit the scope of the present disclosure.

FIG. 2 is a plan view of a substantially rigid instrument;

Figure 3A:
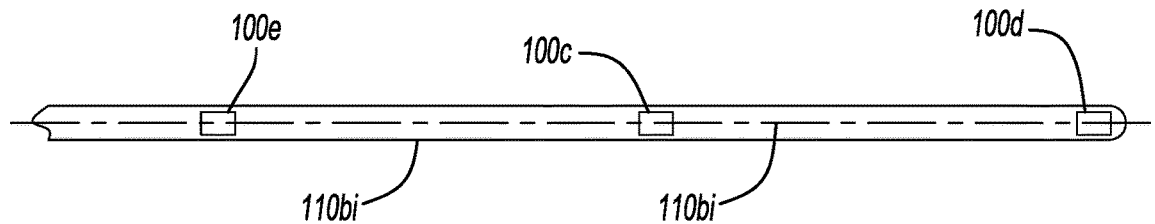
FIG. 3A is a plan illustration of a representation of the flexible instrument, such as on a display.
Figure 3B:
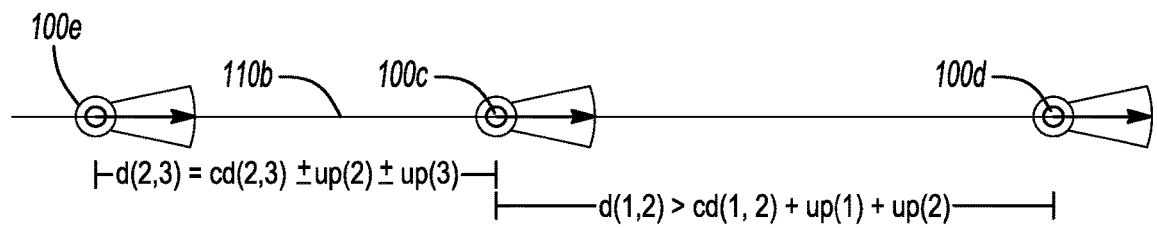
FIG. 3B is a schematic illustration of an improbable navigated position, according to various embodiments.
Figure 3C:
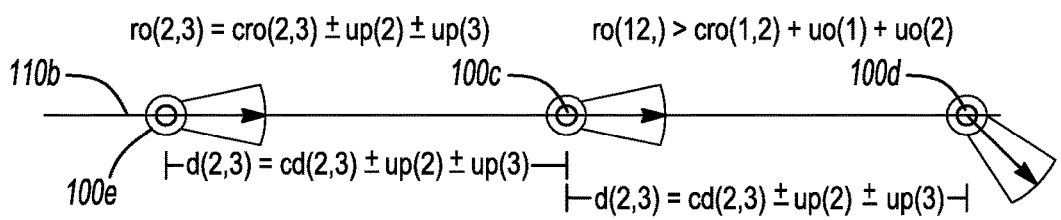
FIG. 3C is a schematic illustration of an improbable navigated position, according to various embodiments.
Figure 3D:
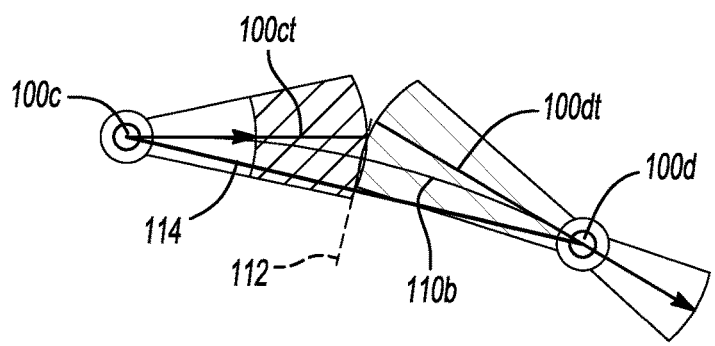
FIG. 3D is a schematic illustration of a first order probable curve navigated curve, according to various embodiments.
Figure 3E:
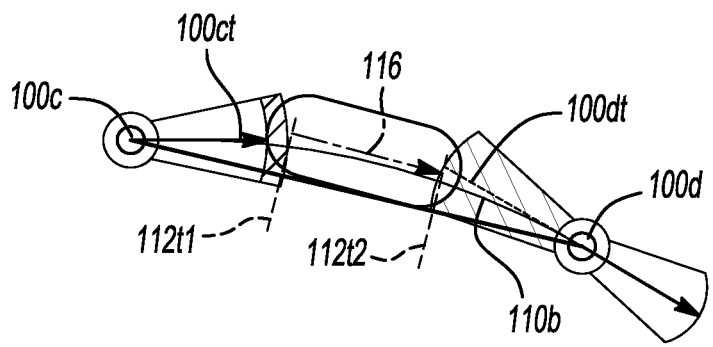
FIG. 3 is a plan view of a flexible instrument.
Figure 3F:
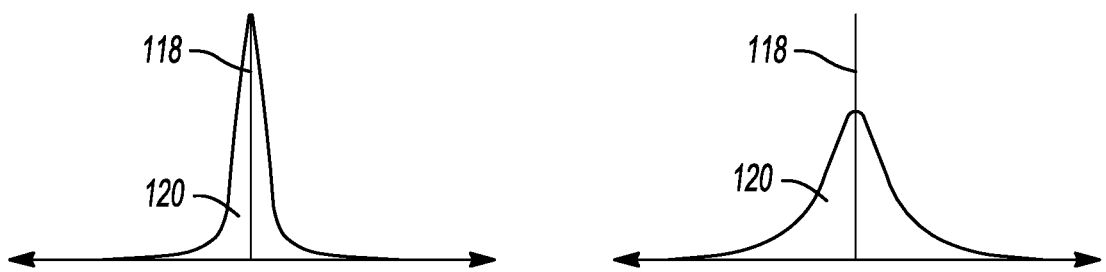
Figure 3G:
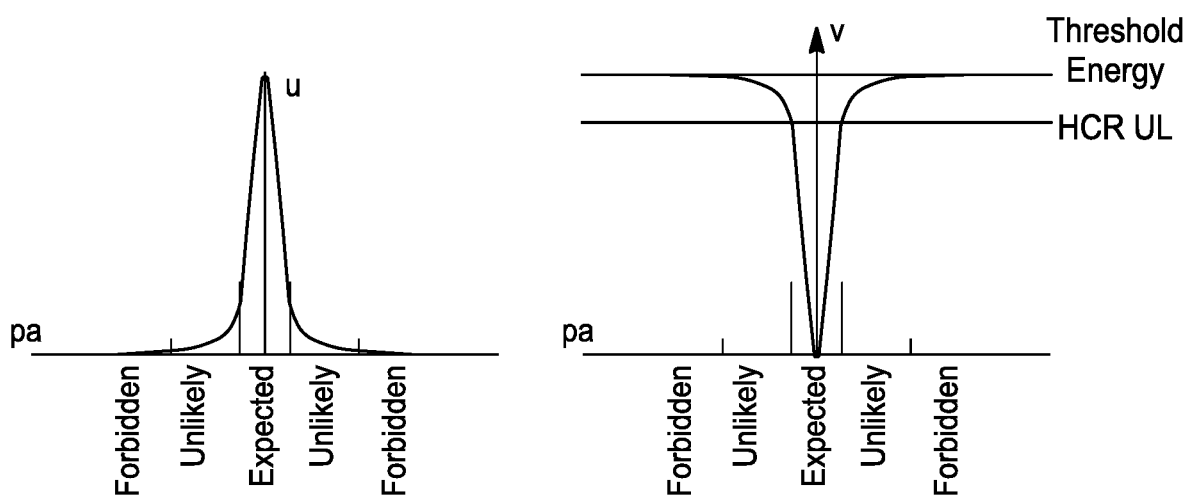
Figure 3H:
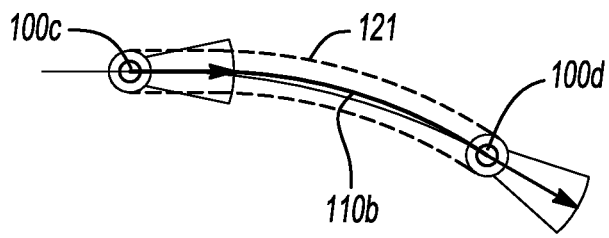
Figure 4:
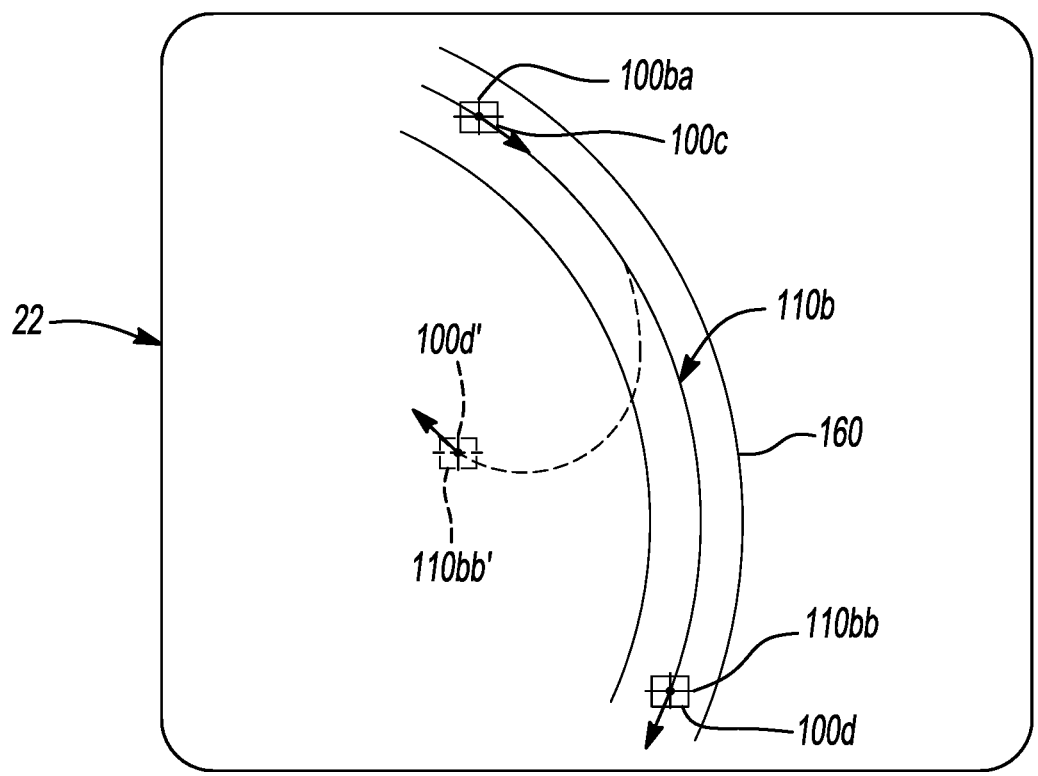
Figure 5:
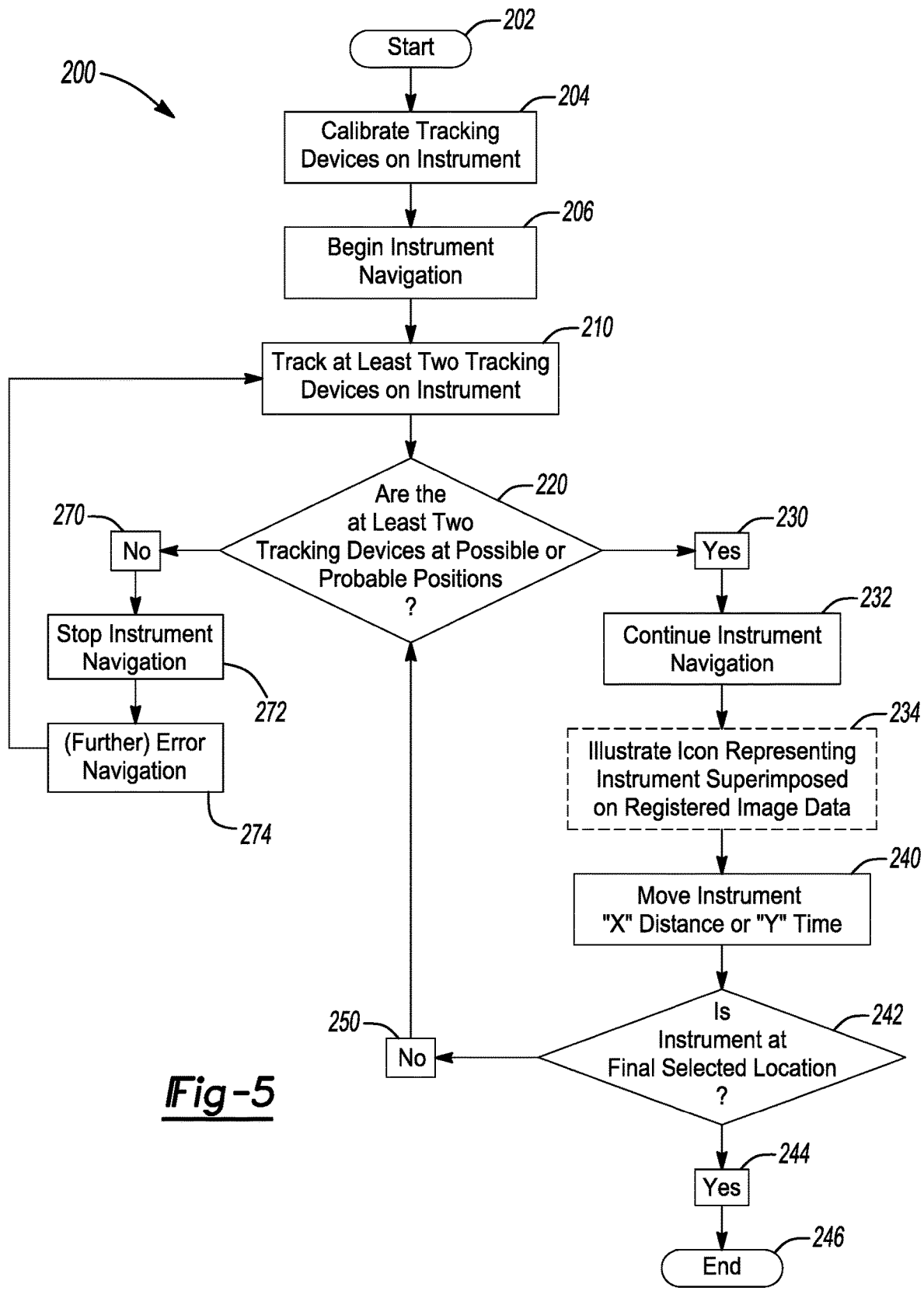

FIG. 3Ea schematic illustration of a second order probable curve navigated curve, according to various embodiments;

FIG. 3F is a graph of location uncertainties and orientation uncertainties;

FIG. 3G is a graph of the uncertainties illustrated in FIG. 3F and related thresholds;

FIG. 3H is a schematic illustration of a probable navigated position determined by bending energy, according to various embodiments;

FIG. 4 is a display screen illustrating image data and navigation data;

FIG. 5 is a flowchart of a method for navigating an instrument; and

Figure 6:
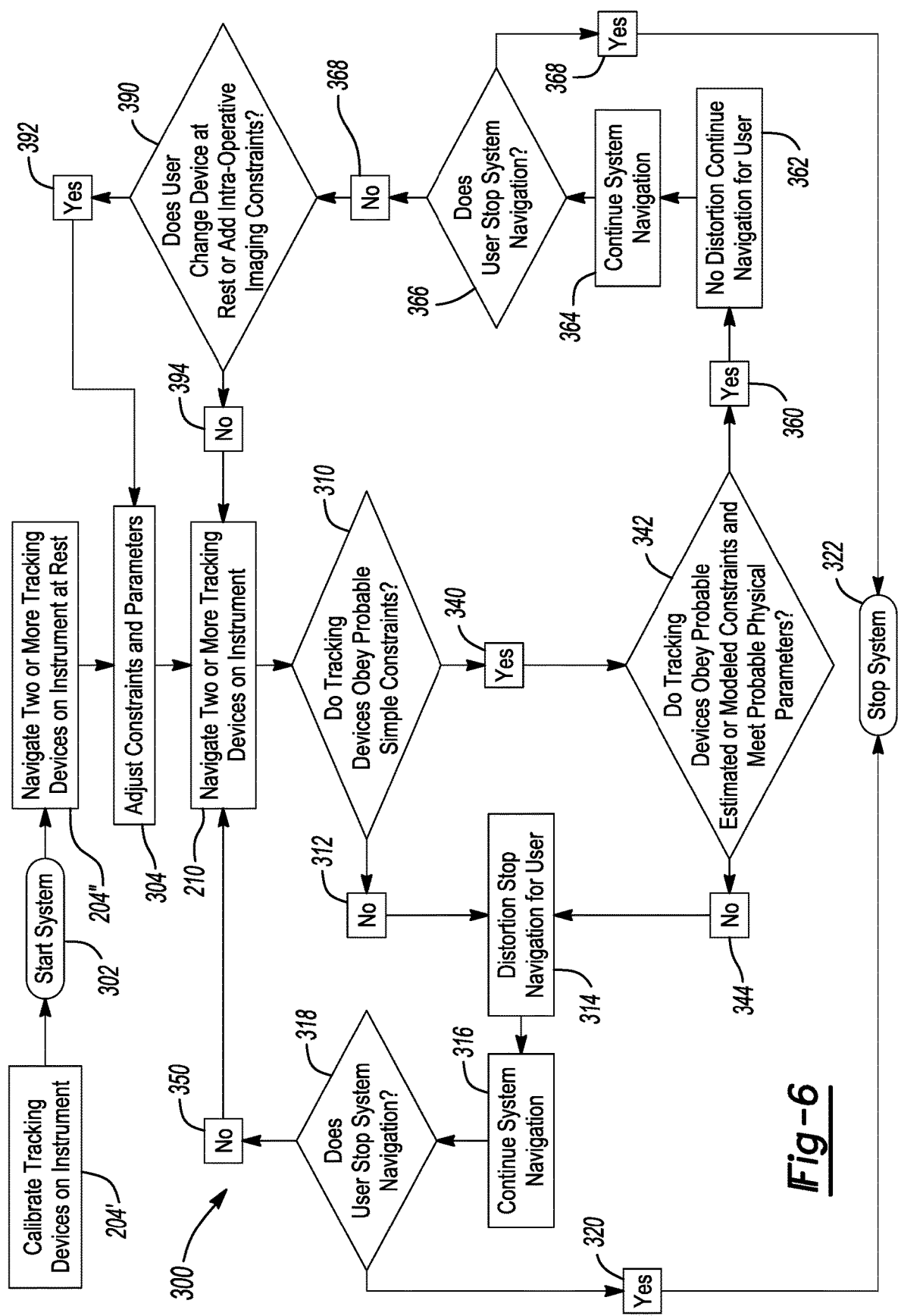

FIG. 6 flowchart of a method for navigating an instrument.

Corresponding reference numerals indicate corresponding parts throughout the several views of the drawings.

DETAILED DESCRIPTION

Example embodiments will now be described more fully with reference to the accompanying drawings.

The following description is merely exemplary in nature and is not intended to limit the present disclosure, application, or uses. It should be understood that throughout the drawings, corresponding reference numerals indicate like or corresponding parts and features.

The present disclosure specifically provides an example of performing a procedure on a subject, such as a human patient. It is understood, however, that the subject invention is not limited to performing a procedure on a patient. For example, a procedure can be performed on an animal subject as well. As a further alternative, the subject disclosure disclosing a device and a method can be performed related to any appropriate volume. For example, a procedure can be performed relative to a volume, relative to a mechanical device or enclosed structure. The volume need not be of a living subject, but can be rather of an inanimate or animate object. In various examples the subject can be an object including an enclosed mechanical device. In various further examples, the subject can be a non-human animal A guided procedure can be performed with a navigation system 20, in FIG. 1. The guided procedure can be any appropriate procedure, such as a neural procedure, a spinal procedure, and an orthopedic procedure. The navigation system 20 can include various components, as will be discussed further herein. The navigation system 20 can allow a user, such as a surgeon 21, to view on a display 22 a relative position of an instrument 110 to a coordinate system. The coordinate system can be made relative to an image, such as in an image guided procedure, or can be registered to a subject 26 only, such as in an imageless procedure. As noted above, the subject can be a human patient or any other appropriate subject.

Briefly, an imageless system can be provided which allows registration of an instrument to subject space alone, rather than both subject space and image space. In an imageless system, image data of the subject 26 need not be acquired at any time. Although image data can be acquired to confirm various locations of instruments or anatomical portions, such image data is not required. Further, the imageless system can be provided to allow for tracking the subject 26 and an instrument relative to the subject 26.

In an exemplary imageless system, a determination of a position of an anatomical structure can be made relative to the instrument and the locations of each can be tracked. For example, a plane of an acetabulum can be determined by touching several points with a tracked instrument. A position of a femur can be determined in a like manner. The position of the relative portions, including the instrument and the anatomical portion, can be displayed on a display, with icons or graphics. The display, however, need not include image data acquired of the patient. One skilled in the art will understand that other data can be provided in an imageless system like atlas data or morphed atlas data. The atlas data can be image data that is generated or generalized from a subject. For example, a brain atlas can be generated based on detail analysis and study of image data of a brain of a selected patient. Nevertheless, an imageless system is merely exemplary and various types of imageless or image based systems can be used, including the image based system discussed below.

It should further be noted that the navigation system 20 can be used to navigate or track generally rigid instruments (i.e. those that are unlikely to bend enough during use in a procedure to unintentionally alter their physical dimensions) including: drill motors, probes, awls, drill bits, large outer diameter (OD) needles, large or inflexible implants, etc. Additionally, tracking a flexible instrument can also occur, especially with a method and system to determine if distortion is present near a tracking device on the flexible instrument. Flexible instruments can include those that either intentionally flex or are not rigid enough to substantially ensure that they will not change configuration during use, the flexible instruments include: catheters, probes, guidewires, small OD needles, small or flexible implants, deep brain stimulators, electrical leads, etc.

Moreover, the instrument can be used in any region of the body. The navigation system 20 and the various instruments 110 can be used in any appropriate procedure, such as one that is generally minimally invasive, arthroscopic, percutaneous, stereotactic, or an open procedure. Although an exemplary navigation system 20 can include an imaging device 28, one skilled in the art will understand that the discussion of the imaging device 28 is merely for clarity of the present discussion and any appropriate imaging system, navigation system, patient specific data, and non-patient specific data can be used. Image data can be captured or obtained at any appropriate time with any appropriate device.

The navigation system 20 can include the optional imaging device 28. The optional imaging device 28 or any appropriate imaging device can be used to acquire pre-, intra-, or post-operative or real-time image data of a patient 26. The illustrated imaging device 28 can be, for example, a fluoroscopic x-ray imaging device that may be configured as a C-arm 28 having an x-ray source 30 and an x-ray receiving section 32. Other imaging devices may be provided and reference herein to the C-arm 28 is not intended to limit the type of imaging device. An optional calibration and tracking target and optional radiation sensors can be provided, as understood by one skilled in the art. Image data may also be acquired using other imaging devices, such as those discussed herein. An example of a fluoroscopic C-arm x-ray device that may be used as the optional imaging device 28 is the "Series 9600 Mobile Digital Imaging System," from OEC Medical Systems, Inc., of Salt Lake City, Utah. Other exemplary fluoroscopes include bi-plane fluoroscopic systems, ceiling fluoroscopic systems, cath-lab fluoroscopic systems, fixed C-arm fluoroscopic systems, isocentric C-arm fluoroscopic systems, 3D fluoroscopic systems, O-arm® imaging system, etc.

An optional imaging device controller 34 can control the imaging device 28 to capture the x-ray images received at the receiving section 32 and store the images for later use. The controller 34 may also be separate from the C-arm 28 and/or control the rotation of the C-arm 28. For example, the C-arm 28 can move in the direction of arrow 28a or rotate about a longitudinal axis 26a of the patient 26, allowing anterior or lateral views of the patient 26 to be imaged. Each of these movements involves rotation about a mechanical axis 36 of the C-arm 28.

The operation of the C-arm 28 is understood by one skilled in the art. Briefly, x-rays can be emitted from the x-ray section 30 and received at the receiving section 32. The receiving section 32 can include a camera that can create the image data from the received x-rays. It will be understood that image data can be created or captured with any appropriate imaging device, such as a magnetic resonance imaging system, a positron emission tomography system, or any appropriate system. It will be further understood that various imaging systems can be calibrated according to various known techniques. Further, an imager tracking device 38' can be provided to track a position of the receiving section 32 of the imaging device 28 at any appropriate time by the navigation system 20.

The image data can then be forwarded from the C-arm controller 34 to a navigation computer and/or processor 40 via a communication system 41. The navigation processor 40 can include a processor that is configured to operate to navigate a procedure, including a general purpose processor or computer executing instructions for navigation. The communication system 41 can be wireless, wired, a hardware data transfer device (e.g. a physical-ROM and/or rewritable flash memory), or any appropriate system. A work station 42 can include the navigation processor 40, the display 22, a user interface 44, and an accessible memory system 46. It will also be understood that the image data is not necessarily first retained in the controller 34, but may be directly transmitted to the workstation 42 or to a tracking system 50, as discussed herein. The workstation 42 can be any appropriate system such as a substantially portable computer and/or processor system with an integrated display 22. The workstation 42 may include a substantially portable computer, such as known laptop or tablet computer configurations, further including ruggedized laptop computer configurations.

The work station 42 provides facilities for displaying the image data as an image on the displays 22, saving, digitally manipulating, or printing a hard copy image of the of the received image data. The user interface 44, which may be a keyboard, mouse, touch pen, touch screen, or other suitable device, allows the user 21 to provide inputs to control the imaging device 28, via the C-arm controller 34, or adjust the display settings of the display 22. The work station 42 can also be used to control and receive data from a coil array controller (CAC)/navigation probe or device interface (NDI) 54/56.

Figure 1:
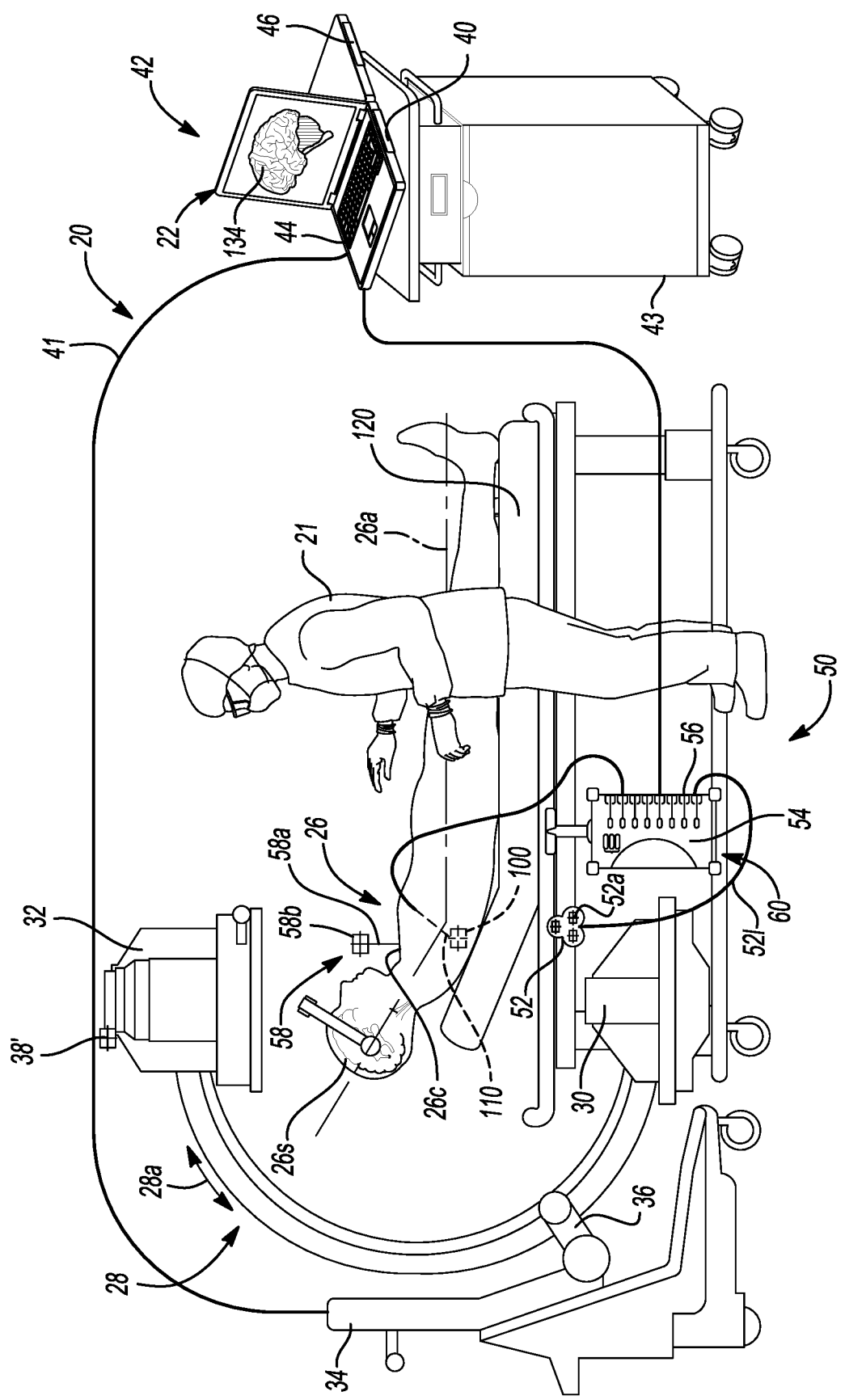
FIG. 1 is an environmental view of an operating room having a tracking system according to various embodiments.

While the optional imaging device 28 is shown in FIG. 1, any other alternative 2D, 3D or 4D imaging modality may also be used. For example, any 2D, 3D or 4D imaging device, such as isocentric fluoroscopy, bi-plane fluoroscopy, ultrasound, computed tomography (CT), multi-slice computed tomography (MSCT), T1 weighted magnetic resonance imaging (MRI), T2 weighted MRI, high frequency ultrasound (HIFU), positron emission tomography (PET), optical coherence tomography (OCT), intra-vascular ultrasound (IVUS), ultrasound, intra-operative CT, single photo emission computed tomography (SPECT), or planar gamma scintigraphy (PGS) may also be used to acquire 2D, 3D or 4D pre- or post-operative and/or real-time images or image data of the patient 28. The images may also be obtained and displayed, generally, in two or three dimensions. In more advanced forms, three-dimensional surface rendering regions of the body that may be rendered or changed in time (fourth dimension) may also be achieved by incorporating patient data or other data from an atlas or anatomical model map or from pre-operative image data captured by MRI, CT, or echocardiography modalities. A more detailed discussion on optical coherence tomography (OCT), is set forth in U.S. Pat. No. 5,740,808, issued Apr. 21, 1998, entitled "Systems And Methods For Guiding Diagnostic Or Therapeutic Devices In Interior Tissue Regions" which is hereby incorporated by reference.

Image datasets from hybrid modalities, such as positron emission tomography (PET) combined with CT, or single photon emission computer tomography (SPECT) combined with CT, can also provide functional image data superimposed onto anatomical data to be used to confidently reach target sites within the patient 26. It should further be noted that the optional imaging device 28, as shown in FIG. 1, provides a virtual bi-plane image using a single-head C-arm fluoroscope as the optional imaging device 28 by simply rotating the C-arm 28 about at least two planes, which could be orthogonal planes to generate two-dimensional images that can be converted to three-dimensional volumetric images. By acquiring images in more than one plane, an icon representing the location of the instrument, such as an impacter, stylet, reamer driver, taps, drill, deep brain stimulators, electrical leads, needles, implants, probes, or other instrument, introduced and advanced in the patient 26, may be superimposed in more than one view on the display 22 allowing simulated bi-plane or even multi-plane views, including two and three-dimensional views.

With continuing reference to FIG. 1, the navigation system 20 can further include the tracking system 50 that includes a localizer 52, (e.g. which can also be referred to as a transmitter array, a tracking array, tracking coils, or coil array and can include a transmitter and/or receiver coil array). One skilled in the art will understand that the coil array 52a can transmit or receive and reference to a transmit coil array herein is merely exemplary and not limiting. The tracking system 50 can further include a coil array controller (CAC) 54 that can have at least one navigation device interface (NDI) 56 for connection of the localizer 52, an instrument tracking device, and a dynamic reference frame 58. The CAC 54 and the at least one NDI 56 (e.g. a communication port, wired or wireless) can be provided in a single substantially small CAC/NDI container 60.

With continuing reference to FIG. 1, the dynamic reference frame 58 can include a dynamic reference frame member 58a and a removable tracking device 58b. Alternatively, the dynamic reference frame 58 can include the tracking device 58b that is formed integrally with the dynamic reference frame member 58a. For example, the tracking device 58b can be connected directly to the patient 26, including a skull 26s of the patient 26 or by some other portion fixed to the patient 26, such as a MAYFIELD® Composite Series Skull Clamp including those sold by Integra LifeSciences Corporation having a place of business at Plainsboro, N.J., USA. One skilled in the art will understand that the tracking device 58b can be any appropriate device and can be an emitter, a receiver, a reflector, a sensor to sense a field, or any other appropriate device that can be tracked by a tracking system including a localizer. Also the tracking device 58b can be wired to the other portions of the system 20 or have a wireless communication therewith, as discussed herein.

The localizer 52 can include that described in U.S. patent application Ser. No. 10/941,782, filed Sep. 15, 2004, now U.S. Pat. App. Pub. No. 2005/0085720, and entitled "METHOD AND APPARATUS FOR SURGICAL NAVIGATION", herein incorporated by reference. The first localizer may also be supplemented and/or replaced with one or more additional localizers, not illustrated, to provide additional fields or breadth of the navigation field. It is understood that the localizer array 52a, according to any of the various embodiments, can transmit signals that are received by the dynamic reference frame 58 and at least one tracking device 100 that is associated with (e.g. connected to) an instrument 110. The tracking device 100 can be associated with the instrument at a location that is generally positioned within the patient 26 during a procedure. The dynamic reference frame 58 and the tracking device 100 can then transmit signals based upon the received/sensed signals of the generated fields from one or more of the localizer 52.

It should further be noted that the entire tracking system 50 or parts of the tracking system 50 may be incorporated into other portions in the operating theatre. Incorporating and/or integrating the tracking system 50, or at least portions thereof, may provide an integrated system. The integrated system can provide for various features such as known or reduced field interference or distortion.

For example, one of the localizers, or any appropriate or selected portion of the tracking system 50, can be incorporated into the imaging device 28. The transmitter coil array 52a can be attached to the receiving section 32 of the C-arm 28. It should be noted, however, that the localizer 52 may also be positioned at any other location as well. For example, the localizer 52 may be positioned at the x-ray source 30. Also, the localizer can be positioned within or atop an operating room (OR) table 120 positioned below the patient 26, on siderails associated with the OR table 120, or positioned on the patient 26 in proximity to the region being navigated, such as on the patient's chest.

The localizer 52, according to various embodiments, can include a coil array 52a that is used in an electromagnetic tracking system. The localizer 52 may also be positioned in the items being navigated, further discussed herein, including the instrument 110. Also, the coil array 52a of the localizer 52 can include a plurality of coils that are each operable to generate distinct electromagnetic fields into the navigation region of the patient 26, which is sometimes referred to as patient space. Electromagnetic systems are generally described in U.S. Pat. No. 5,913,820, entitled "Position Location System," issued Jun. 22, 1999 and U.S. Pat. No. 5,592,939, entitled "Method and System for Navigating a Catheter Probe," issued Jan. 14, 1997, each of which are hereby incorporated by reference.

The coil array 52a is controlled or driven by the coil array controller (CAC) 54. The CAC 54 can transmit a signal with a transmission line 521, 110al, and 110bl to the respective localizers 52. The coil array 52a of each localizer 52 can have more than one coil that is driven by the coil array controller 54 in a time division multiplex, a frequency division multiplex manner, or selected appropriate manner. Each coil array 52a can include at least one coil for generating a field and/or receiving a field. In various embodiments, each coil array 52a can include at least three substantially orthogonal coils to generate three substantially orthogonal fields. In various embodiments, each coil array 52a can include a plurality of coils in any suitable configuration (e.g. non-orthogonal) to generate any selected diverse fields. In this regard, each coil of the coil array 52a may be driven separately at a distinct time or all of the coils may be driven simultaneously with each being driven by a different frequency, as discussed further herein.

Upon driving the coils in the coil array 52a with the coil array controller 54, electromagnetic fields are generated within the patient 26 in the area where the medical procedure is being performed, which is again sometimes referred to as patient space. The electromagnetic fields generated in the patient space induce currents in the tracking devices 100 positioned on or in the instrument 110. These induced signals from the instrument 110 are delivered to the navigation device interface 56 and can be forwarded to the coil array controller 54 and/or the processor 40. The navigation probe interface 56 may provide all the necessary electrical isolation for the navigation system 20, as discussed herein. The NDI 56 can also include amplifiers, filters and buffers to directly interface with the tracking devices 58b, 100. Alternatively, the tracking devices 58b, 100, or any other appropriate portion, may employ a wireless communications channel, such as that disclosed in U.S. Pat. No. 6,474,341, entitled "Surgical Communication Power System," issued Nov. 5, 2002, herein incorporated by reference, as opposed to being coupled with a physical transmission line to the NDI 56.

When the navigation system 20 uses an EM based tracking system, various portions of the navigation system 20, such as tracking devices 58b, 100 are equipped with at least one and generally more coils that are operable with the EM localizer arrays 52. Alternatively, the tracking system may be a hybrid system that includes components from various tracking systems such as optical, acoustic, etc.

The EM tracking device 100 on the instrument 110 can be in a handle or inserter that interconnects with an attachment and may assist in placing an implant or in driving a portion. The instrument 110 can include a graspable or manipulable portion at a proximal end and the tracking sensor device that can be fixed near the manipulable portion of the instrument 110 or at a distal working end, as discussed herein. The tracking device 100 can include an electromagnetic sensor to sense the electromagnetic field generated by the localizer 52 that can induce a current in the tracking device 100. As illustrated in FIG. 1, and discussed further herein, the tracking device 100 associated with the instrument 110 can also be placed completely or partially within the patient 26.

The dynamic reference frame (DRF) 58 of the tracking system 50 can also be coupled to the NDI 56 to forward the information to the CAC 54 and/or the processor 40. The DRF 58, according to various embodiments, may include a small magnetic and/or electromagnetic field detector as the tracking device 58b. The dynamic reference frame 58 may be fixed to the patient 26 adjacent to the region where navigation is occurring so that any movement of the patient 26 is detected as relative motion between the localizer 52 and the dynamic reference frame 58. The dynamic reference frame 58 can be interconnected with the patient 26 in any appropriate manner, including those discussed herein. Any relative motion is forwarded to the coil array controller 54, which updates registration correlation and maintains accurate navigation, further discussed herein. If the dynamic reference frame 58 is electromagnetic it can be configured as a one, a pair, trio, or selected number of selectively oriented coils. For example, if more than one coil is used all of the coils may be mutually orthogonal with each having the same center or may be configured in any other non-coaxial or co-axial coil configurations. Also, one or more coils may be used to sense substantially diverse fields from a localizer.

The dynamic reference frame 58 may be affixed externally to the patient 26, adjacent to the region of navigation, such as on the patient's skull 26s, etc. The dynamic reference frame 58 can be affixed to the patient's skin, by way of a selected adhesive patch and/or a tensioning system. The dynamic reference frame 58 may also be removably attachable at or to a fiducial marker. Fiducial markers can be anatomical landmarks and/or artificial members attached or positioned on the patient's 26 body. The dynamic reference frame 58 can be connected to a bone portion of the anatomy, such as the skull 26s or a chest wall 26c. The bone portion can be adjacent, the area of the procedure, the bone of the procedure, or any appropriate bone portion.

Briefly, the navigation system 20 operates as follows. The navigation system 20 creates a map between all points in the image data or image space and the corresponding points in the patient's anatomy in patient space. After this map is established, the image space and patient space are registered. In other words, registration is the process of determining how to correlate a position (which is can be used in the current disclosure to refer to a location and an orientation) in image space with a corresponding position in real or patient space. Based on the registration, the navigation system can also be used to illustrate a position of the instrument 110 relative to an image of the patient 26, such as super-imposed thereon. For example, the instrument can be illustrated relative to the proposed trajectory and/or the determined anatomical target. The work station 42 alone and/or in combination with the coil array controller 54 and/or the C-arm controller 34 can identify the corresponding point on the pre-acquired image or atlas model relative to the tracked instrument 110 and display the position on display 22 and relative to an image 134 that is based on or generated with acquired or accessed image data. Each of the systems (i.e. the workstation, the CAC, and the C-arm controller) can be incorporated into a single system or executed by a single processor. This identification is known as navigation or localization. An icon representing the localized point or instruments (which can also include models of the instruments) is shown on the display 22 within several two-dimensional image planes, as well as on three and four dimensional images and models.

To register the patient 26 to the image 134, the user 21 may use point registration by selecting and storing particular points from the pre-acquired images and then touching the corresponding points on the patient's anatomy with a pointer probe or any appropriate tracked device, such as the instrument 110. The navigation system 20 analyzes the relationship between the two sets of points that are selected and computes a match, which allows for a determination of a correlation of every point in the image data or image space with its corresponding point on the patient's anatomy or the patient space.

The points that are selected to perform registration or form a map are the fiducial markers, such as anatomical or artificial landmarks. Again, the fiducial markers are identifiable on the images and identifiable and accessible on the patient 26. The fiducial markers can be artificial landmarks that are positioned on the patient 26 or anatomical landmarks that can be easily identified in the image data. The artificial fiducial markers can also form part of the dynamic reference frame 58, such as those disclosed in U.S. Pat. No. 6,381,485, entitled "Registration of Human Anatomy Integrated for Electromagnetic Localization," issued Apr. 30, 2002, incorporated herein by reference. It will be understood that any appropriate number of the fiducial markers can be provided with and/or separate from the DRF 58.

The navigation system 20 may also perform registration using anatomic surface information or path information as is known in the art (and may be referred to as auto-registration). The navigation system 20 may also perform 2D to 3D registration by utilizing the acquired 2D images to register 3D volume images by use of contour algorithms, point algorithms or density comparison algorithms, as is known in the art. An exemplary 2D to 3D registration procedure is set forth in U.S. Ser. No. 10/644,680, filed on Aug. 20, 2003, now U.S. Pat. App. Pub. No. 2004-0215071, entitled "Method and Apparatus for Performing 2D to 3D Registration", hereby incorporated by reference.

In order to maintain registration accuracy, the navigation system 20 continuously can track the position of the patient 26 during registration and navigation with the dynamic reference frame 58. This is because the patient 26, dynamic reference frame 58, and localizer 52 may all move during the procedure, even when this movement is not desired. Alternatively the patient 26 may be held immobile once the registration has occurred, such as with a head holder. Therefore, if the navigation system 20 did not track the position of the patient 26 or area of the anatomy, any patient movement after registration would result in inaccurate navigation within that image. The dynamic reference frame 58 allows the tracking system 50 to track the anatomy and can be used in registration. Because the dynamic reference frame 58 is rigidly fixed to the patient 26, any movement of the anatomy or the localizer 52 is detected as the relative motion between the localizer 52 and the dynamic reference frame 58. This relative motion is communicated to the coil array controller 54 and/or the processor 48, via the NDI 56, which updates the registration correlation to thereby maintain accurate navigation.

The dynamic reference frame 58 can be affixed to any appropriate portion of the patient 26, and can be used to register the patient to the image data, as discussed above. For example, when a procedure is being performed relative to the skull or cranium 26s, the dynamic reference frame 58 can be interconnected with the cranium 26s. The dynamic reference frame 58 can be interconnected with the cranium 26s in any appropriate manner, such as those discussed herein according to various embodiments.

The tracking system 50, if it is using an electromagnetic tracking assembly, can work by positioning the localizer 52 adjacent to the patient space to generate an electromagnetic (EM) field, which can be low energy and also generally referred to as a navigation field. Because every point in the navigation field or patient space is associated with a unique field strength and direction, the electromagnetic tracking system 50 can determine the position (which can include location and orientation) of the instrument 110 by measuring the field strength and direction, or components thereof, at the tracking device 100 location. The dynamic reference frame 58 is fixed to the patient 26 to identify the location of the patient 26 in the navigation field. The electromagnetic tracking system 50 continuously recomputes the relative position of the dynamic reference frame 58 and the instrument 110 during localization and relates this spatial information to patient registration data to enable image guidance of the instrument 110 within and/or relative to the patient 26.

To obtain a maximum accuracy it can be selected to fix the dynamic reference frame 58 in each of at least 6 degrees of freedom. Thus, the dynamic reference frame 58 or any tracking device, such as the tracking device 100, can be fixed relative to axial motion X, translational motion Y, rotational motion Z, yaw, pitch, and roll relative to the portion of the patient 26 to which it is attached. Any appropriate coordinate system can be used to describe the various degrees of freedom. Fixing the dynamic reference frame relative to the patient 26 in this manner can assist in maintaining maximum accuracy of the navigation system 20.

The instrument 110 can be any appropriate instrument (e.g., a catheter, a probe, a guide, etc.) and can be used for various mechanisms and methods, such as delivering a material to a selected portion of the patient 26, such as within the cranium 26s. The material can be any appropriate material such as a bioactive material, a pharmacological material, a contrast agent, or any appropriate material. As discussed further herein, the instrument 110 can be precisely positioned (including location and orientation) via the navigation system 20 and otherwise used to achieve a protocol for positioning the material relative to the patient 26 in any appropriate manner, such as within the cranium 26s. The instrument 110 may also include a brain probe to perform deep brain stimulation.

As discussed above, an EM field can be generated by the EM localizer 52. The EM field is generated to define a navigation field. The navigation field can, however, be distorted by various distorting objects including the operating table 120, the imaging device 28, various instruments, etc.

The instrument 110, according to various embodiments, can be a substantially rigid probe 110a, illustrated in FIG. 2. The probe 110a can have a tracking device 100a associated therewith, such as the tracking device 100a attached to a handle or graspable portion 140 of the probe 110a. The probe 110a can also include a probe tip 142 that can be used to engage a portion of the subject, such as a fiducial marker or location for registration, as discussed above. The rigidity of the probe 110a can be based on physical and/or material properties of the probe 110a. Generally, the substantially rigid probe can be that the probe 110a.

The probe tip 142 can be substantially rigidly connected and/or oriented relative to the handle 140 via an elongated probe body 144. The probe body 144 can have various physical properties, such as a dimension (e.g., width) and/or material selection, to substantially ensure that the tip 142 is maintained at substantially one position, including three-dimensional location and three-dimensional orientation, relative to the tracking device 100a during a procedure. The rigidity of the elongated shaft 144 can ensure that the geometric position of the tip 142 relative to the tracking device 100a remains unchanged during a procedure. The rigidity of the probe 110b that maintains the tip 142 in a selected position relative to the handle 140 can be based on characteristics of the probe 110a, including material selection, thickness, etc. The generally unchanged tip position relative to the handle 140 can include, however, a change from an initial or calibrated position that is greater than a sensing or navigation error or some multiple thereof. Generally, however, movement of the tip is constrained within the system given various attributes of the instrument, such as the rigidity of the probe 110b.

Thus, the rigidity provides a constraint of possible or probable locations of the tracking device 100a relative to the probe tip 142. Accordingly, if a determination is ever made that the tip 142 is at a different position from an initial or calibrated position relative to the tracking device 100a, the navigation system 20 can provide a signal to the user 21. Signals can include various informational signals such as a tactile signal, a visual signal on a digital display on the display device 22, an audible signal, or an inactivation of the display device 22.

Generally, the tip 142 can be calibrated to be at a determined position, which can be a three-dimensional position, but is illustrated on the display as a distance 142x from the center of the tracking device 100a. Because the location of the probe tip 142 is constrained relative to the tracking device 100a, the probe 110a can touch a known point (i.e. at a known position in patient space) in the navigation field during a procedure and the tracked position of the tracking device 100a relative to the tip 142 (which is at the known position), can be used to determine whether the tracking system 50 is operating properly or if an error is occurring. Errors can include a distortion of the EM field.

After a calibration that can be used to determine the location of the tracking device 100a relative to other points on the probe 110a, such as the probe tip 142, the probe 110a can be used. During use of the probe 110a, such as during movement of the probe 110a, if the tracking system 50 determines that the distance between the tip 142 and the tracking device 100a is changing a determination that distortion is present can be made. In various embodiments, movement of the tip 142 relative to the tracking device 100a can be determined with a second tracking device 100b that can be provided on the shaft 144. The two tracking devices 100a and 100b can be tracked with the tracking system 50.

Because the probe 110a is rigid, the location of the two tracking devices 100a, 100b relative to one another is constrained. That is that they are not able to move relative to one another. Thus, the rigidity of the shaft 144 substantially ensures and constrains that the true tracking devices 100a and 100b are at substantially fixed positions relative to one another during a procedure. The constraints can also include rotational fixation, thus a torsional resistance of the probe 110a can provide a constraint on the relative locations of the two tracking devices 100a, 100b.

Regarding the rigid probe 110b, movement of the two tracking devices 100a, 100b relative to one another can be used as a metric to determine if an error is occurring. Accordingly, if the tracking system 50 determines that two tracking devices are moving relative to one another, a determination that distortion is present or other fault in the tracking system is occurring can be made. If an error is determined then the user 21 can be signaled with an appropriate signal based upon this determination. It is understood, however, that selected error and small amount of noise can be tolerated and even illustrated with the display. For example, a "fat" icon can be used to illustrate a position of the instrument 110a. That is, a tracked position of the tracking devices can be determined and the displayed icon can be made larger relative to the displayed anatomy to account for the error and small amount of noise. Thus, if the probe 110a is 1 mm thick it can be illustrated to be 1.5 mm thick to illustrate the tolerated error.

With reference to FIG. 3, a flexible instrument 110b is illustrated. The instrument 110b can be a flexible instrument, such as a guide wire or catheter, and can have any appropriate selected length. The flexible instrument 110b can have a length, or a length of a selected portion, that extends between a first end 150 and a second end 152, such as a distal tip. Positioned on the flexible instrument 110b along its length can be one or more tracking devices, such as a first tracking device 100c at a first tracking device location and a second tracking device 100d at a second tracking device location. The two tracking devices 110c and 100d can be tracked with a tracking system 50, as discussed above. It is understood that more than two tracking devices can also be provided with the instrument 110b, such as including a third tracking device 110e or any selected number, as illustrated in FIG. 3A. A position of the flexible instrument 110b can then be illustrated on the display device 22 relative to the image data 134, such as with an icon, similar to the inflexible instrument 110a. It is understood that any appropriate number of icons can be used to illustrate the instrument 110b, such as one or more icons representing the specific tracking devices 100c, 100d, and 100e and a separate instrument icon 110bi (e.g. one of a different color or opacity) can be provided to overlay the tracking device icons, as illustrated in FIG. 3A.

The flexible instrument 110b, therefore, differs substantially only from the inflexible instrument 110a in that the flexible instrument 110b can either intentionally or unintentionally be flexed or change orientation or shape during a procedure. Generally, the flexible instrument 110a may elastically flex from an at rest position and configuration with the imposition of a force, but then may return to its at rest position and configuration when the force is removed. For example, the distance or length of the flexible instrument 110b between the two tracking devices 100c and 100d can be intentionally or unintentionally changed during a procedure. For example, if the flexible instrument 110b is flexed during use, a first distance 110xii, illustrated in phantom, can be different than a second distance 110xi, as illustrated in FIG. 3. The first distance 110xii can be a maximum distance, which can be a calibrated at-rest distance, while the second distance 110xi can be a flexed distance. The distance 110xi can be used as a zeroth order estimate of an arc length between the two tracking devices 100c and 100d. As discussed herein, higher order estimates can be used to determine whether the tracking devices 100c and 100d are at probable relative locations and whether distortion in the navigation field is probable. It is understood here, and throughout the present disclosure, that certain uncertainties in the tracking and navigation systems can be considered and tolerated. Thus, it is understood that the distances 110xi and 110xii include a level of uncertainty that is plus or minus the navigated lengths.

Although the flexible instrument 110b can flex or bend, the flexible instrument 110b can be limited in other movements, such as compression, stretching, or twisting (i.e. torsion constraints). For example, the flexible instrument 110b can be formed of a material that does not compress or stretch during use, or will not likely stretch or compress during use, even if it can bend or flex, as illustrated in FIG. 3. Thus, the maximum distance 110xii can be a distance constraint on the location of the two tracking devices 110c, 110d relative to one another. As discussed herein, it can be determined whether the distance 110xi is an appropriate distance between the two tracking devices 100c and 100d based upon a possible bending of the flexible instrument 110b. In other words, a determination that compression or stretching is occurring can be a determination that an error is present, as discussed herein. Similar constraints regarding torsion can be used to determine that distortion is probable.

Other constraints based on physical and/or material properties of the probe 110b can include the torsional resistance, modulus of elasticity, thickness of the probe 110b, etc. The properties of the probe 110b can constrain the minimum distance between the two tracking devices 100c, 100d and/or relative rotational orientations between the two tracking devices 100c, 100d. These constraints can provide a metric to determine whether there is an error (e.g. navigation field distortion) when tracking the probe 100b.

Various determination techniques, such as "energy" of bending (also referred to herein as bending energy), can be used to determine whether the distance 110xi (which can include an uncertainty, as discussed above) is an appropriate or probable distance between the two tracking devices 100c and 100d. Due to the uncertainties, the presently disclosed system may determine probable bending energies. Moreover, other freedom of motions can include compression, torsion, etc. in probable energy calculations. A calculation of energies, including the bending energy, can be based on the physical calculations, such as those disclosed in Methods of Mathematical Physics, vol. I., R. Courant and D. Hilbert, Interscience, New York, 1953, incorporated herein by reference. The bending energy can be a calculation based on known or determined constraints on the relative locations of the two tracking devise 100c, 100d based on the properties of the flexible instrument 110b.

The appropriateness or probability of the two tracking devices 100c and 100d being at any determined relative position can be made based upon the bending energy and an "at rest" distance 110xii, illustrated in phantom in FIG. 3, including any known uncertainties of the tracking the positions to determine the distance 110xii. For example, a calibrated at rest distance 110xii can be determined at a selected time. For example, the flexible instrument 110b can be placed in the navigation field on a flat surface and the determined position of the two tracking devices 100c and 100d can be made. Also, the "at rest" or straight distance can be physically measured and stored in the storage device 46 for retrieval. The at-rest distance can be the maximum possible distance that the two tracking devices 100c, 100d can be apart given the uncertainties in tracking the tracking devices 100c and 100d and the physical constraints of the instrument 110b.

As the flexible instrument 110b can bend in three-dimensions, an arc length of the flexible instrument 110b between the two tracking devices 100c and 100d can also be provided as a constraint. Materials that form the flexible instrument 110b can be used to identify, either theoretically or experimentally, possible and/or probable bending radii lengths of the instrument 110b between the two tracking devices 100c and 100d. For example, a radius 110r can be determined as a maximum radius between the tracking device 100c and an end point 110bp on the instrument 110b and a second minimum radius 100rd can be determined as a minimum radius between the bend point 110bp and the second tracking device 100d. The position of the bend point 110bp can be based upon the materials, dimensions, and other constraints of the instrument 110b. The bend point 110bp, however may not be directly determinable during navigation. Nevertheless, an estimated radius of curvature could be determined based on determined radii from each of the tracking devices 100c, 100d to selected midplanes or midpoints based on a magnitude of difference in orientation of the two tracking devices 100c, 100d over the estimated distance between the two tracking devices. It is understood that other degrees of freedom can also supply constraints that can be analyzed to determine probable relative positions of two or more tracking devices.

The distance 110xi can be used to estimate an arc length of the instrument between the two tracking devices 100c and 100d. In addition, the distance 110xi can be used as a simple constraint on the relative location of the tracking devices 100c and 100d. For example, given that the instrument 110b cannot extend, if a determined distance between the two tracking devices 100c and 100d is measured to be more than the distance 110xii, a determination can be made that the two tracking devices are not at a possible or probable position and the navigation field may be distorted due to a distorting element. Another simple constraint can be that the tracked relative orientations of the two tracking devices 100c and 100d can be compared. Based on torsional resistance a determination can be made whether the tracked orientation is probable. As discussed herein, the simple constraint can be used in a system or process (e.g. an algorithm) executed by a processor to determine that a distortion is present. It is understood that certain uncertainties in the tracking and navigation systems can be considered, tolerated, and accommodated within these arc length and curvature estimates.

The possible or probable bending energies can be based on physical constraints and properties of the instrument 110b. These physical constraints and properties may be modeled theoretically or measured experimentally. For example, based on the physical properties of the instrument 110b such as modulus of elasticity, different amounts of energy are required to bend the instrument 110b and move the two tracking devices to different distances apart creating the radii 110rc, 110rd. These bending energies can then be used to determine the probability of the calculated distance 110xi and/or radii 110rc, 110rd between the tracking devices 100c, and 100d during a procedure. As discussed herein, the greater the bending energy the less likely that the tracked tracking devices 100c, 100d are at the tracked locations. For example, a very short distance between the two tracking devices 100c and 100d would require a very large bending energy to be applied and it would be unlikely that a selected high bending energy would be applied. It is understood, however, that different instruments may have different bending energy probabilities based on their respective properties. For example, a thin plastic catheter may be more flexible than a thick guidewire. Thus, a greater bending energy may be required to bend the thick guidewire to the same radius of curvature as the thin plastic catheter. These differences can be accounted for with an appropriate algorithm, as discussed herein. It is also understood, as noted herein, that other degrees of freedom can also be used to determine a probable relative location of tracking devices. For example, torsional and compression properties of the instrument 110b can be used to determine limits on relative motion of two or more tracking devices.

As the flexible instrument 110b can bend in three-dimensions, an arc length of the flexible instrument 110b between the two tracking devices 100c and 100d can also be provided as a constraint. This arc length distance 110xii can be a maximum distance, which can be a calibrated at-rest distance. The distance 110xi can be used as a zeroth order estimate of an arc length between the two tracking devices 100c and 100d. The positions and orientations of the tracking devices 100c and 100d can be used to construct planes and points midway between the tracking devices 100c and 100d. The point 100bp displays an example midpoint. The distance 100rc from the tracking device 100c to mid-point 100bp and the distance 100rd from the mid-points 100bp to the tracking device 100d can be used as a first order estimate of an arc length between the tracking devices 100c and 100d. The magnitude of the difference between orientations of the tracking devices 100c and 100d over the estimated arc length between positions for tracking devices 100c and 100d can be used as an estimate of curvature and can be used to construct a second order estimate of an arc length between the tracking devices 100c and 100d. The positions and orientations of the tracking devices can be used in physically based energy calculations, discussed herein, to determine a higher order or continuous estimate of the of an arc length between the tracking devices 100c and 100d.

These arc length estimates can be compared to the arc length constraint to determine if distortions are present. As the flexible instrument 110b can bend in three-dimensions, a maximum curvature of the flexible instrument 110b between the two tracking devices 100c and 100d can also be provided as a constraint. This maximum curvature can depend upon instrument materials and construction and can be modeled theoretically or measured experimentally. The above discrete estimated arc lengths can be used to estimate a radius of curvature which is inversely proportional to curvature. The physically based energy calculation can be used to estimate the curvature directly. These curvature estimates can be compared to the maximum curvature constraint to determine if distortions are present. It is understood that certain uncertainties in the tracking and navigation systems can be considered, tolerated, and accommodated within these arc length and curvature estimates. It is also understood that other degrees of freedom and motion, such as torsion and compression, may also supply constraints that can be analyzed to determine probable relative positions of two or more tracking devices.

As discussed briefly above, the at-rest position, illustrated in dashed lines, can provide an initial determination of the position of the tracking devices 100c and 100d relative to one another. It is also understood that the tracking devices 100c and 100d can be tracked as a three dimensional space position, including location and orientation. Accordingly, the orientation of the tracking devices 100c and 100d can be determined relative to one another in the at-rest position. This can allow a determination of an orientation of a curve or bend of the flexible instrument 110b. For example, the bend of the flexible instrument 110b can be in three dimensions where the bend may occur in substantially two planes relative to the flexible instrument 110b.

Determining possible or probable energy of bending or radii can assist in determining whether distortion is present in the navigation field. The tracking devices 100c and 100d and the tracking devices 100a and 100b of the inflexible instrument 110a can be affected by distortions in a navigation field, as discussed above. The distortions can be caused by various conducting or magnetic elements that are positioned in or near the EM field generated by the localizer 52. For example, when the patient 26 is positioned on the operating table 120 and the instrument 110a or 110b is positioned within the patient 26, the instrument may move towards the operating table 120. When the instrument is near the operating table 120, the operating table may cause distortion in the EM field that is sensed by the respective tracking devices 100a-100d on the respective instruments 110a, 110b. For example, the tracking device 100d near a distal tip of the instrument 110b can be moved near the operating room table 120 and distortion in the sensed field can occur. The distortion can cause the determined position of the tracking devices 100a-100d to be incorrect.

If the determined positions of the tracking devices are incorrect, then the navigation of the instrument may be improper within the subject. Accordingly, as discussed above, if the tracking devices are determined to be at positions that are impossible or improbable, a determination that the navigation is improper can be made and an indication can be made to the user to stop or end navigation. The indication to stop can be a warning to the user 21. The navigation system 20, however, may continue navigation and determine that distortion is no longer present after a passage of time, as discussed in FIG. 6 herein. According to various techniques, an energy determination can be made to determine whether the tracking devices fixed to the instrument 110b is proper.

In one example, an improbable or impossible change in the tracking devices 100c and 100d can occur it is appears that they have twisted relative to one another. As discussed above, an at-rest or calibration period can be used to initially determine the position of the tracking devices 100c and 100d relative to one another. If the flexible instrument 110b is not able to twist, then a change in orientation of the tracking devices 100c and 100d relative to one another, due to twisting of the instrument, would generally not occur. Accordingly, if twisting of the tracking devices 100c and 100d relative to one other is determined by tracking the tracking devices 100c and 100d, then an error in the navigation field or in the determined location of the tracking devices can be made.

Also, the instrument may be only able to bend to a certain degree due to physical constraints (e.g. materials, size of the instrument, etc.) during a procedure. Therefore, a "least energy" curve can be used to determine the probability that a determined curve of the instrument 110b is probable. For example, an amount of energy required to force the flexible instrument 110b to curve can be calculated or determined based upon a determined position and/or amount of the curve of the instrument 110b. The energy of the curve can be an arbitrary amount, such as an amount required to curve the instrument 110b a selected amount having a selected radius or arc length based upon material constants of the flexible instrument 110b, including a modulus of elasticity, a wire constants, and other known pre-determined factors. The constants of the flexible instrument 110b can be stored in the memory device 46 and used for the determination of the bending energy of the curve. The greater the bending energy calculated the less probable that the curve is actually present in the instrument and the greater the likelihood that an error is present, such as a distorted EM field in the navigation field.

An algorithm for determining a curve can be based upon the tracked orientation of the tracking devices 100c and 100d along with the known physical constraints of the instrument 110b. The algorithms can include the calculations of the radii from the tracking devices and determination of curve lengths based on methods discussed in Methods of Mathematical Physics, vol. I., R. Courant and D. Hilbert, Interscience, New York, 1953 and The Curve of Least Energy, B. K. P Horn, ACM Trans. Math. SW, vol. 9 pp. 441-460, 1983. The tracked or determined positions of the tracking devices 100c and 100d can be used to identify the radii 100rc and 100rd from each of the respective tracking devices 100c and 100d.

A calculation of an arc length can also be used to determine whether tracked locations of the tracking devices 100c and 100d are probable. If the calculated arc length is not generally probable based on the physical constants of the instrument 110b, then a determination that an error is present, such as the navigation field is distorted. The arc length can be determined based on the tracked location of the tracking devices 100c and 100d and the distance 110xi.

As discussed above, in general, various physical constraints of the instrument 110b can be used to determine whether the relative locations of two or more tracking devices 100c and 100d are probable. Based on the determined probability the navigation system 20 can notify or warn the user 21. Although the system can continue to navigate the instrument to attempt to determine when the distorting feature has been removed from a position to effect one or more of the tracking devices 100c, 100d.

In various embodiments, a simple constraint can be included. As illustrated in FIGS. 3 and 3A the tracking devices can have at-rest positions that are at an unchanging location (e.g. distance apart) and relative orientation. As illustrated in FIG. 3B, due to possible distortion a distance (d(1,2)) between the tracking devices 100c and 100d can be greater than the calibrated at-rest distance plus any uncertainty of position (up) regarding a tracked location the tracking device 100c (up(1)) and the tracking device 100d (up(2)). A metric of this constraint violation can be set to effectively detect EM field distortions and appropriately prevent inaccurate navigation.

In various embodiments, a simple constraint also holds regarding relative orientation (ro) of the tracking device 100c relative to the tracking device 100d. Again, uncertainty of the tracked orientation of the tracking device 100c ((uo(1)) and an uncertainty regarding a tracked orientation of the tracking device 100d (uo(2)) can be accounted. A tracked orientation that is above the calibrated and expected relative orientation can be used to stop navigation for the user 21. The expected relative orientation can be based on physical constraints of the instrument 110b. Again, a metric of the relative orientation constraint violation can be set to effectively detect EM field distortions and appropriately prevent inaccurate navigation.

In addition to the simple constraints, complex or modeling constraints can be used to determine probable flexing of the instrument 110b. The flexible instrument 110b can flex to form an arc between two or more of the tracking devices 100c and 100d. Given the acceptable and probable arc length formation of the instrument 110b, a simple constraint that the orientation of two tracking devices are not within a calibrated relative orientation may not be sufficient or acceptable to determine possible field distortion. For example, when the instrument is flexed as illustrated in FIG. 3, the tracking device 100d may be above a calibrated orientation relative to the tracking device 100c. Nevertheless, the instrument 110b is able to bend to form the arc length and it is not indicative of a distorted field.

Distortion detection methods can extend the simple constraints to other constraints, such as arc length between tracking devices 100c and 100d. As flex deformations of the instrument 110b affect the multiple tracking devices 100c and 100d in ways that maintain arc length, a modeling metric of this comparison can be set to accept flex deformations. As field distortions can affect the multiple tracking devices 100c and 100d in ways that violate the modeling constraint, the metric of this comparison can be set to effectively detect field distortions and appropriately prevent inaccurate navigation. Other exemplary constraints include, but are not limited to, relative tracking device orientations for compressible instruments or relative tracking device positions for rotatable instruments.

Again consider the tracking devices 100c, 100d, and 100e placed along and/or within the instrument 110b with their orientations aligned with a long axis 110b1 of the instrument 110b. The navigated positions of these tracking devices 100c, 100d, and 100e approximate points along a three dimensional curve. The navigated orientations of these tracking devices 100c, 100d, and 100e approximate tangents at these points along this curve. The curve and its properties can be approximated according to various techniques.

For example, as illustrated in FIG. 3D, a discrete first order approximation of the curve can be modeled using the navigated location points and orientations of the tracking devices 100c, 100d, and 100e. An example technique approximates the curve by extending a tangent 100ct from the tracking device 100c and a tangent 100dt from the tracking device 100d towards a bisecting normal plane 112 of a relative position vector 114 between the two tracking devices 100c and 100d and connecting the intersections of the tangents 100ct, 100dt in this plane 112. This technique can also incorporate the uncertainties in locations and orientations and determine extended overlap volumes. A rough approximate curve arc length can then be determined based on the location of the intersection of the tangents 100ct and 100dt with the plane 112 and the relative position vector 114.

An increase in an accuracy of the modeled curve can be obtained with a second order approximation. An example, as illustrated in FIG. 3E, of the technique roughly approximates curvature by a difference in tangent vectors from each of the tracking devices 100c and 100d. The technique approximates a curve by extending the first tangent 100ct towards a first trisecting normal plane 112t1 of the relative position vector 114 and extending the second tangent 100ct towards a second trisecting normal plane 112t2 of the relative position vector 114. The technique then connects the intersections of the tangents 100ct and 100dt in these planes 112t1 and 112t2 with an average tangent 116 that is an average of the two tangents 100ct and 100dt extended from the first to second normal planes 112t1 and 112t2.

Further exemplary techniques and algorithms for curve estimation are found in D. J. Williams and M. Shah, "A Fast Algorithm for Active Contours and Curvature Estimation", CVGIP: Image Understanding, vol. 55, pp. 14-26 1992, incorporated herein by reference.

In further modeling techniques, parameterizing flexibility via a curvature energy parameter is possible. The parameterizing flexibility includes accounting for variable flexibility of various and different instruments. Curvature parameters can be determined with material elastic moduli and/or empirical testing. This and other instrument specific parameters can be added to a navigation calibration information. Thus, the current distortion detection method extends simple and other constraints to include estimated parameters compared to probable values given calibrated parameters of the instrument 110b. As an example, curvature between two or more tracking devices 100c and 100d provides a parameter for flexible instruments, such as guide wires. As flex deformations of the instrument 110b affect the multiple tracking devices 100c and 100d in ways that increase curvature in expected manners, a metric of this comparison can be set to accept flex deformations.

As discussed herein, user specified re-calibration positions of the tracking devices 100c and 100d can also be incorporated. As an example, a user 21 may want to plastically deform a guide wire between tracking devices 100c and 100d. The user 21 could interact with the navigation software to measure the instrument at a new, plastically deformed rest configuration. The navigation system 20 could then adjust the previous calibration information and apply the distortion detection method to the re-calibrated instrument. The navigation system 20 can include software to allow user input of the plastically deformed at-rest position.

Continuous approximation of a curve between two or more of the tracking devices 100c and 100d can also be made using the navigated points and orientations. An example family of techniques approximates the curve by interpolating amongst points and tangents subject to various constraints and boundary conditions. These interpolations can incorporate uncertainties in positions and orientations. These techniques then estimate arc length and curvature via secondary calculation along the interpolating curves. Examples of general interpolations may be found in Curves and Surfaces for CAGD, A Practical Guide, 5th ed., G. Farin, Morgan-Kaufmann, Burlington, 2002, incorporated herein by reference. Examples of specific techniques may be found in Numerical Method for Extracting an Arc Length Parameterization from Parametric Curves, R. J. Sharpe and R. W. Thorne, Computer-Aided Design, vol. 14 pp. 79-81, 1982; The Length of Bézier Curves, J Gravesen, Graphics Gems V, p199-205, Academic Press, Boston, 1995; and Constraint-Based LN Curves, Y. J. Ahn and C. M. Hoffmann, Computer Aided Geometric Design, vol. 29 pp. 30-40, 2012, all incorporated herein by reference.

Another family of techniques approximates the curve by minimizing functionals amongst points and tangents subject to various constraints and boundary conditions. These interpolations can easily incorporate uncertainties in positions and orientations. These techniques directly minimize curvature and incorporate arc length constraints. Examples of general variational techniques may be found in Methods of Mathematical Physics, vol. I., R. Courant and D. Hilbert, Interscience, New York, 1953, incorporated herein by reference. Examples of specific techniques may be found in The Curve of Least Energy, B. K. P Horn, ACM Trans. Math. SW, vol. 9 pp. 441-460, 1983 and Path Planning for Minimal Energy Curves of Constant Length, M. Moll and L. E. Kavraki, Proc. of the IEEE Int. Conf. on Rob. Auto., pp. 2826-2831, 2004, all incorporated herein by reference.

A third family of techniques combines the first and second families. This third family approximates the curve by interpolating implicitly minimal energy curves amongst points and tangents subject to various constraints and boundary conditions. Examples of specific techniques may be found in Energy Formulations of Algebraic Splines, C. L. Bajaj, et. al. Computer Aided Geometric Design, vol. 16 pp. 39-59, 1999; Approximation of Minimum Energy Curves, R. Qu and J. Ye, Applied Math. and Comp., vol. 108, pp 153-166, 2000; and Efficient Approximation of Minimum Energy Curves with Interpolatory Constraints, R. Qu and J. Ye, Applied Math. and Comp., vol. 109, pp 151-166, 2000, all incorporated herein by reference.

As an example of continuous estimation of a curve, an appropriately constructed, constrained, probability weighted energy functional can be minimized to approximate a curve amongst points and tangents, such as those defined relative to the instrument 110b as illustrated in FIGS. 3D and 3E. An energy functional EQ. 1 can be built starting with a bending energy that depends upon curvature $\kappa$.

$$E_B = \int \left(\frac{1}{2}\right)\kappa^2$$

$$ds = \int \frac{dT}{ds} \circ \frac{dT}{ds} ds$$

Here, s denotes the curve parameter and T denotes the curve tangents. We can constrain the functional EQ. 1 to an arc length $c_{al}$ via a Lagrange multiplier $c_{al}$ in EQ. 2.

$$E_{BC} = \int [\kappa^2 + \lambda_{al}(1-c_{al})] ds$$

Subject to EQ. 3

$$\nabla_{\lambda_{al}} E_{BC} = 0$$

We can implement additional constraints via additional Lagrange terms. Such constraints can include, but are not limited to, curve intersections at measured points and curve tangent alignment with measured tangents at measured points in EQ. 4.

$$E_C = \Sigma \int [\lambda_k (g_k - c_k)] ds$$

We can also incorporate uncertainty distributions into this energy functional EQ.4.

Consider again the uncertainty in position distribution around p and the uncertainty in orientation distribution around o. Each uncertainty distribution will have support over a three dimensional domain. Each distribution may be decomposed along independent principal axes. Each distribution will depend upon the position and orientation within the navigation volume. We illustrate example distributions in more detail in with a cross section 118 along a principal axis and around centers 120, illustrated in FIG. 3F.

To incorporate these uncertainty distributions, illustrated in FIG. 3F, into the energy functional EQ. 5, the distributions can be turned upside down and scales with an appropriate energy threshold. The energy threshold can be based upon known or determined physical constraints of the instrument 110b. For example, a thin flexible plastic catheter may have a greater threshold than a thick guidewire. The threshold values can be used to identify energies that are expected and unlikely. Also, a threshold can be used to identify an energy that is forbidden and can be a threshold that is used to identify distortion in a navigation field. Appropriate simplified representations, e.g. walled quadratics, of these energy transformed uncertainty distributions can also be used.

Variations "m" around tracking locations of the tracking devices 100c and 100d and the tangents 100ct and 100dt, constraints can be appropriately softened, and explicit energy transformed uncertainty terms "v" can be added to incorporate uncertainty distributions in EQ. 5

$$E_T = \int_{v_0(m_{p0})}^{v_N(m_{pN})} [\kappa^2 + \lambda_{al}(1 - c_{al}(v_{p0}, v_{pN}))]ds + \sum \int [\lambda_k(g_k - c_k(v_k))]ds + \sum \int [v_j]dm_j$$

These functional terms can be transformed to common parameterizations to efficiently minimize the total energy functional EQ. 5 to find a model for a constrained and probable curve of the instrument 110b. It is understood that this example is for a flexible, but not compressible, extendable, or twistable instrument 110b. However, compression, torsion, or other such degrees of freedom can be incorporated into the energy functional EQ. 1 and constrain them as appropriate. As illustrated in FIG. 3H, a modeled approximation of the locations and orientations of the tracking devices 100c and 100d is illustrated along with an approximated arc length and minimized total energy 121. As illustrated, the actual locations and orientations of the tracking devices 100c and 100d are on the instrument 110b and the tracked locations of the tracking devices 100c and 100d are within the constrained energy determination.

Also a combination of a minimization with certain interpolations can be made. These techniques approximate the curve by interpolating an implicitly minimal energy curves amongst points and tangents subject to various constraints, boundary conditions, and probability weights. The above described calculations can be incorporated into a computer or processor executable algorithm to detect distortion by using the above and other continuous approximations to determine probable violations against calibration and constraint information, such as physical constraint parameters, to provide a distortion detection method for non-rigid instruments.

Illustrated in FIGS. 3D, 3E, and 3H are instances when the navigation system 20 has tracked the tracking devices to probable potions (including location and orientation). It is understood, therefore, that the instances when the navigated positions of the tracking devices are not at probable positions then the illustration of those instances would illustrate the tracking devices not aligned along the long axis of the instrument and/or the arc length is too short. An arc length being too short can include an unacceptable bending energy determination. The display device 22 can display both the probable and the improbable navigated positions of the tracking devices 100c and 100d and/or the instrument 110b.

In addition to identifying or determining a minimum or least energy curve, a selected (e.g. "maximum") energy can also be identified along with a possible arc length and intra-operative information to further constrain the energy calculation of the curve. For example, as illustrated in FIG. 4, the flexible instrument 110b can be illustrated relative to a vein 160 of the subject 26. The illustration of the vein 160, or other portion within the subject 26, can be displayed on the display device 22. As discussed above, the display device can illustrate image data of the subject 26 and the vein 160 can be a portion of the image data. Accordingly, a substantially physical constraint of the flexible instrument 110b can be determined.

In one example, the calculation can be constrained by the walls of the vein 160 based on an assumption that the flexible instrument 110b would not pass through a wall of the vein 160, given various characteristics of the flexible instrument 110b. It is understood that the vein 160 is provided here as an example, but that other procedure or operational constraints can be determined. For example, the probe 110b would not pass through bone, a metal wall, move quickly in a viscous material, or other procedural constraints that can be determined.

Accordingly, the curve of the flexible instrument 110b may be limited by the physical constraints of the vein 160. The arc of the vein 160 can be determined by measuring the length of the arc using the image data acquired of the subject 26. An arc length between points 110ba and 110bb on the flexible instrument 110b can then be measured based upon the tracking devices 100c and 100d. Generally, the arc length can be identified or determined between the point 110ba determined at tracking device 100c and point 110bb determined at the tracking device 100d). If the arc length between 110ba and 110bb is outside of a range possible due to the physical constraints of the vein 160, then a determination of an error, such as a distorted navigation field can be made. In addition when calculating the energy of the curve, the "maximum energy" would be that energy that is allowed to provide a maximum curve within the physical constraints of the subject 26 due to the position of the instrument within the vein 160. It is understood that other constraints can also be identified or determined intra-operatively, such as the length of the flexible instrument 110b positioned within the subject 26, and other exemplary constraints.

As an example, illustrated in FIG. 4, in phantom, a tracked position of the tracking device 100d' can be related to an arc end 110bb', this position exterior to the vessel and substantially closer to the first tracking device 100c then shown in solid lines. If the navigation system 20 determines that the tracking device 110d is at the position 110d' and the arc length is determined to have the end point 110bb', then the navigation can be terminated due to an error, such as possible distortion in the navigation field. In particular, as illustrated in FIG. 4, the flexible instrument 110b would be required to have exited the vessel 160 to be at the position illustrated in phantom. As discussed above, a physical constraint can be included in a determination of the bending energy to form the arc length illustrated in the phantom line and therefore can be related to an error, such as due to distortion of a navigation field.

Moreover, weighting can be used to determine the possibility or probability of distortion. For example, a higher or greater amount of weighting can be provided per unit of "energy". For example, a threshold energy value can be identified and a weighting can be applied above the threshold energy amount. For example, each unit of energy greater than the threshold can be additionally weighted in the energy calculation. Again, a maximum energy can be determined for identifying whether the flexible instrument 110b is being improperly tracked due to identifying a curve that is improbable or impossible for the flexible instrument 110b.

It is understood, as illustrated in FIG. 3, that the flexible instrument 110b can be bent due to a direction of the user 21. Accordingly, it is understood that the determination of the energy of the bend can also be pre-calibrated or re-calibrated based upon the user 21 bending the flexible instrument 110b. Further, the user 21 can pre-bend the flexible instrument 110b to assist in moving the flexible instrument 110b within the patient 26. For example, the user 21 may pre-bend a guide wire to assist in moving the guide wire through a vascular throughout the subject 26. The pre-bent instrument will generally flex and return to the bent configuration created by the user 21.

It is also understood that the determination of a possible distortion in the navigation field can be applied to any plurality of alterable instruments. As illustrated above, the flexible instrument 110b is a substantially elongated member that is one piece. It is understood, however, that a two-piece instrument could also be provided. The two-piece instrument may have a hinge that hingedly connects two members such that the two members can bend or move relative to one another. The tracking devices 110c, 110d can be positioned on the two members on either side of the hinge. The possible bending or range of motion of the hinge can be preloaded into the memory system 46 and if tracked locations of the tracking devise 100c and 100d is outside of the range of motion of the hinge, then the possibility of distortion can be made and the navigation can end.

Additionally, the tracking devices 100c and 100d can be positioned on two portions of an instrument that move relative to one another. For example, a guide wire positioned within a catheter that is being tracked in the navigation space. A maximum distance that the guide wire can move or be positioned relative to the catheter (i.e. a distance between the two tracking devices associated with the guide wire and the catheter) can be determined and measured to identify if possible distortion is occurring if the maximum distance is exceeded.

Accordingly, it is understood that a single-piece flexible instrument is merely exemplary of an instrument that can have a geometry that is altered during a procedure. However, the position of the tracking devices 100c and 100d relative to one another can be tracked and used to determine whether the tracked location of the tracking devices 100c and 100d are beyond the physical limit of the flexible instrument 110b to determine that navigation is improper, for example, due to distortion of the navigation field. Generally, the tracking devices 100c and 100d are tracked substantially simultaneously for making the determination to ensure that both tracking devices are sensing the same navigation field.

With reference to FIG. 5, and continuing reference to previous FIGS. 1-4, a flowchart 200 is illustrated. The flowchart 200 relates to a process that can be implemented as a computer or processor executable program to assist in determining whether the tracked locations of the tracking devices are proper or if an error has occurred, such as a distortion in the navigation field. The method 200 begins in start block 202 and progresses in block 204 to calibrating the tracking devices on the instrument.

Calibration can occur at any time prior to positioning the instrument, such as the flexible instrument 110b, in a subject. Calibration can include determining locations of the various tracking devices to ends or other locations on the instrument 110b, such as a determined distance from a distal tip. Calibration can also include determination of an uncertainty in determining a location and an orientation. Thus, there may be uncertainty regarding a navigated location of the tracking devices 100c, 100d which can be accounted for with the system.

At an appropriate time, such as before or following calibration but prior to tracking in block 210, the location constraints can be loaded or accessed by the system. The location constraints can be constraints regarding possible locations of the respective tracking devise 100c and 100d. The constraints can be based on constraints of the probe 110b, including torsional resistance, length between tracking devices, elasticity, etc. The constraints, therefore, can be used to indicate the limitations or probable limitations of movement of the tracking devise 100c and 100d on the flexible instrument 110b. The constraints can be used to determine the bending energy. The bending energy, then, as discussed below, can be used to determine the probability of the instrument being bent as determined or that a possible error is present in the navigation field. At a selected threshold the error can be signaled. The threshold can vary based upon the physical constraints of the instrument 110b. As noted above, the instrument 110b can be very flexible, such as a thin plastic catheters, or relatively inflexible, such as a thick guide wire. Thus, the threshold can be predetermined, but can be dependent upon the specific constraints of the instrument 110b.

As discussed above, an at-rest calibration determination of the position, including location and orientation of the tracking devices 100c and 100d relative to the instrument 110b, can be made. That calibration can occur in a factory setting substantially immediately after manufacturing, particularly when the tracking devices are fixed in or relative to the flexible instrument in an immovable manner. Nevertheless, it is understood that the user 21 can also calibrate the tracking devices at any appropriate time prior to insertion of the instrument 110b in the subject 26.

After calibration in block 204, instrument navigation can begin in block 206. As discussed above, instrument navigation can include positioning the instrument in a navigation field generated by the localizer 52 to offer tracking of the tracking devices associated with the flexible instrument 110b. The beginning of the navigation in block 206 can lead to tracking at least two tracking devices in block 210. Tracking at least two tracking devices allows for a determination of two points (generally at a center or some portion of the tracking device) on the instrument 110b, as discussed above. Generally, the two tracking devices are tracked substantially simultaneously. For example, the navigation field can be sensed at the same time for tracking both of the tracking devices.

The two points can be used to determine arc lengths, bending energies, distances between two tracking devices, and the appearance of twisting, stretching, or compression, and the like, as also discussed above. Tracking a single tracking device may be appropriate if an instrument is substantially rigid, but if the instrument is the flexible instrument 110b, tracking two tracking devices allows the navigation system 20 to determine two points for making the above-described calculations. Again, it is understood that the processor system 42 of the navigation system 20 can perform the necessary calculations by executing generally known mathematical programs or geometric programs for determining the geometric locations of the tracking devices relative to one another. It is also understood that the tracked information can be forwarded to a separate processing system for calculation of the arc lengths, and the like.

After the two tracking devices are tracked in block 210, a determination can be made in block 220 of at least determine whether the two tracking devices are at possible or probable positions. If the two tracking devices are at possible or probable positions, as discussed above, via determining an arc length or an energy of bending, then the yes path can be followed through yes block 230 and navigation can be continued in block 232. It is possible, as discussed above, to illustrate an icon representing the instrument super-imposed on registered image in block 234. As illustrated in FIG. 4, the position of the instrument 110b can be illustrated relative to a vessel 160 on the display device 22. It is understood, however, that the flexible instrument 110b can be any appropriate flexible instrument and can be illustrated relative to the appropriate navigated position relative to the subject 26 and super-imposed on the image data 134.

The instrument can then be moved for an "x" distance or "y" time in block 240. That is, the instrument can be moved after the initial determination of whether the tracking devices are at possible or probable positions in block 220. For example, the instrument can be moved a selected tracked distance, such as about 5 millimeters (mm). Additionally, the instrument can be moved for a selected time, such as about 20 milliseconds. After moving the instrument for a selected time or tracked distance, a determination of whether the instrument is at a final selected location can be made in block 242. If the instrument is at the final selected location then a yes path can be followed through yes block 244 and the navigated procedure can end in block 246. It is understood, however, that during selected procedures, such as a surgical procedure, merely positioning the tracked instrument at a final location does not end the surgical procedure, but can end a navigated portion of the surgical procedure or at least a positioning navigated portion of the surgical procedure. It is understood that navigation can still occur during the performance of a selected procedure, such as ablation of cardiac tissue.

If it is determined that the instrument is not at a final selected location in block 242, then a no path 250 can be followed to the determination block of whether the tracking devices are at possible or probable positions in block 220. Accordingly, it is understood that an iterative or loop can occur for determining whether possible or probable positions of the tracking devices is being tracked. Thus, determining whether the tracking devices are at possible or probable positions can be a substantially continuous process to determine whether error is present, such as field distortion is present in the navigation field during an entire navigated procedure.

Returning to block 220, if the determination in block 220 is that the tracking devices are at impossible or improbable positions, then the no block 270 can be followed. Navigation can then be stopped in block 272, such as by providing a signal to the user 21 that navigation is improper. One signal can include removing an image from the display 22 such that a viewing of a tracked location of the instrument 110*b* cannot be made.

Once navigation is stopped in block 272, various error mitigating error steps can occur in block 274. Error mitigating steps in block 274 can include repositioning the patient 26 relative to any possible distorting elements or features (e.g., a surgical instrument or support structures), removing the tracked instrument to a previous location, completely withdrawing the navigated instrument, or other possible mitigating steps.

After at least an initial mitigating step has occurred in block 274, then a tracking of the tracking devices can again occur in block 210 to make a determination of whether the tracked devices are at possible or probable positions in block 220. If the no block 270 is again followed, the navigation can again be stopped in block 272 and further mitigating steps (e.g. additional or different) can occur in block 274. Accordingly, it is also understood that the determination of whether the tracked devices are at possible or probable positions and following the no loop can be used to determine whether the probe 110*b* is ever at a probable position within the navigation field. The method 200, therefore, allows continual assurance that the instrument 110*b*, including the tracking devices 100*c* and 100*d*, are at possible or probable positions.

Accordingly, the method 200 can be used to determine whether the tracked devices 100*c* and 100*d* on the instrument 110*b* are at possible or probable positions. As discussed above, various techniques can be instituted as executable programs or algorithms by the processing system 42 to make the determination in block 220. As discussed above, a bending energy or arc length can be used to determine whether the instrument 110*b* is tracked at a possible or probable position within the navigation field due to various constraints of the flexible instrument 110*b*. As discussed above, the various constraints (i.e. those that are known or determined and input or accessed by the tracking and/or navigation system) can include wire constants, modulus of elasticity, and other physical features of the instrument 110*b*. Additionally, as discussed above, various physical constraints of the position of the instrument 110*b* can also be used to determine whether the calculated energy of the bending is related to possible or probable positions of the tracking devices 100*c* and 100*d*.

It is understood that the method 200, incorporating the various energy calculations discussed above, can be used to determine whether the flexible instrument is at a possible or probable positions due to tracking the tracking devices 100*c* and 100*d*. The tracking devices 100*c* and 100*d* may be at impossible or improbable tracked positions dues to a distortion of the navigation field or errors induced in the tracking of the tracking devices 100*c* and 100*d*. The metrics of the error determination, according to the method 200, can then be used to assist in stopping or ending navigation to ensure that the navigation does not proceed under false or erroneous tracked locations of the tracking devices 100*c* and 100*d*. Also, though bending and a radius determination is disclosed as an exemplary embodiment, it is understood that other physical parameterizable energies can also be used to determine whether a tracked location is improbable. Other energies can include torsion, rotation, etc.

It is further understood, however, that the method 200 can incorporate the various known constraints of the probe 110*b* to determine whether the probe 110*b*, or at least the portions that have the tracking devices 100*c*, 100*d*, are at possible locations. For example, based on an elasticity of the probe 110*b* it can be determined whether the probe 110*b* can achieve the calculated distance 110*xi*. If a constraint is that the probe 110*b* cannot twist, then if the tracking system tracks twisting the navigation can be stopped. In addition, if it is determined that a minimum distance for the distance 110*xi* is "a" then if a distance of less than "a" is tracked, the navigation can be stopped. Moreover, the closer that the distance 110*xi* gets to "a" the more likely it can be determined that the probe 110*b* is at an improbable location and a distortion may be present.

With reference to FIG. 6, a method 300 for determining whether distortion is present and/or navigating an instrument, particularly the non-rigid instrument 110*b* discussed above, illustrated. The method 300 can include portions that are similar to those included in method 200 and similar reference numerals will be used to describe those blocks and repeated discussion thereof will not be included.

The method 300 can begin with calibrating the tracking devices on the instrument in block 204'. Calibrating the tracking devices on the instrument can be identical to calibrating the tracking devices on the instrument in block 204. Calibration in block 204 and 204' can also include determining, such as by measuring, a position of one or more tracking devices relative to a distal and/or proximal tip of the instrument 110b or some other portion of the instrument 110b. The navigation system can then be started in block 302.

Starting the system in block 302 can include initiating navigation, as is generally understood in the art including with the AxiEM® navigation system sold by Medtronic Navigation, Inc. Once the system is started in block 302, navigation of two or more tracking devices on the instrument 110b while the instrument is at rest can occur in block 204″. The navigation of the instrument at rest in block 204″ can be similar to calibrating the tracking devices discussed above in block 204. The navigation of the two or more tracking devices when the instrument is at rest can be used to determine at rest tracking device positions (including locations and orientations) relative to each other and other instrument features, such as the total length of the instrument, a position of a distal end relative to a closest tracking device and the like.

Accordingly, calibrating the tracking devices in block 204′ can include determining the amount of uncertainty regarding a specific location and a specific orientation of a tracking device, as discussed above. Navigating the two or more tracking devices when the instrument is at rest can further include providing calibrating information regarding the tracking device locations and orientations on the tracked instrument 110b and an initial set-up of the instrument 110b. That is, that the instrument 110b can bend under a force from an at-rest position, but then return to the at rest position (including a shape of various portions of the instrument) when no force is applied. Accordingly, the at-rest navigation in block 204″ can assist in determining the at-rest shape of the instrument 110b when no force is applied to the instrument 110b.

After the instrument is navigated at rest in block 204″, adjusting constraints and parameters in block 304 can occur. The constraints and parameters that are adjusted can include those that area entered or input by a user. They can include maximum sensor separation distances, instrument elastic moduli, and further include specific navigation system uncertainties regarding a tracked or navigated location and orientation of the tracking devices. Thus, the user can adjust constraints and parameters to assist in determining whether a navigated location of two or more tracking devices on the instrument 110b are at probable locations using the techniques discussed above and in the method 300, as discussed further herein.

Once the constraints and parameters are input in block 304, a navigation of two or more tracking devices on the instrument can occur in block 210. The navigation can be substantially identical to the tracking two or more tracking devices in block 210 discussed above. Generally, the navigation in block 210 can include tracking the instrument 110b and illustrating a location of the instrument 110b relative to a registered image or on an imageless display.

After beginning navigation in block 210, a first decision block of whether the tracking devices obey probable simple constraints can be made in block 310. The simple constraints can include those discussed above, including whether the distance or orientation between any selected two tracking devices or selected related groups of the tracking devices are outside of expected or calibrated values. An example of violation of a simple constraint can be whether a distance between a first tracking device and a second tracking device is greater than a calibrated and expected distance, including any input uncertainties. Further, the simple constraints can include whether one or more tracking devices are at an unexpected or outside of the calibrated value regarding orientation relative to one another.

If the determination that the tracking devices do not obey the simple constraints in block 310, the NO-path through block 312 can be followed to make a determination that distortion may be present and to stop navigation for a user in block 314. Stopping navigation for a user in block 314 can include providing the alerts to the user that a navigation error may be occurring, this can include not illustrating a navigated position of the instrument 110b. System navigation can, however, continue in block 316, including continuing to navigate the instrument if the user moves the instrument. Even if the display 24 is no longer showing a navigated position the user can move the instrument 110b or portions relative to it, such as withdrawing the instrument or removing any possible distorting structures, such as a secondary or external instrument. Continuing system navigation can allow the system to determine if a distortion has been removed. As the system continues navigation in block 316, a decision block of whether the user ends navigation in block 318 is made. If it is determined that the user has stopped navigation, such as based on the notification from the navigation system, the system can stop the block 322. This can end the use of the navigation system or allow a user to complete withdrawing the instrument from the navigation field and restart navigation at a later time.

If the decision block 310 is determined that the tracking devices do obey probable simple constraints, then a YES-path 340 can be followed to a second decision block of whether the tracking devices obey probable estimated or modeled constraints and meet the probable physical parameters in block 342. The modeled constraints and probable physical parameters include those discussed above, such as first and second order modeling and a bending energy determination for the instrument 110b. As discussed above, the modeling can include a determination of a bending energy between two or more tracking devices on the instrument 110b. If the determination that the tracking devices do not obey the estimated or modeled constraints and probable physical parameters, then a NO-block 344 can be followed to stop navigation for the user in block 314. The system can then follow the method 300 to continue system navigation in block 316 and determine whether the user stops navigation at 318.

If the user does not stop navigation in block 318, based upon any NO-path from either the decision block 310 regarding simple constraints or the decision 342 regarding estimated model or physical constraints, then a NO-path of 350 can be followed to navigate two or more tracking devices in block 210. Accordingly, navigation can continue if a user does not stop navigation. Navigation can continue and a determined location of the instrument 110b can be illustrated based on the distorted navigation field on the display device 24 or based upon a user's knowledge.

If it is determined that the tracking devices do obey the probable estimated and modeled constraints in block 342, then a YES-path can be followed through block 360 to make a determination that no distortion is occurring and navigation can continue for a user in block 362. System navigation can then further continue in block 364 to a decision block of whether a user stops navigation in block 366. If a user does stop navigation in block 366, the system can follow a YES-path through block 368 to stop the system in block 322, as discussed above.

If a user does not stop navigation in block 366, however, a NO-path can be followed through block 380 to a determination block of whether a user changes device at rest configuration or adds additional intra-operative imaging constraints in block 390. As discussed above, as illustrated in FIG. 4, intra-operative imaging constraints can be used to assist in further determining whether tracking devices are obeying simple constraints or model constraints. The modeled constraints evaluated in decision block 342 can be based upon the intra-operative imaging.

If the user does change a device at rest configuration or an intra-operative imaging constraints a YES-path through block 392 can be followed and the navigation of the tracking instrument at-rest in block 204" can be re-evaluated. The method 300 can then follow through block 304 to adjust constraints and parameters and begin navigation of the tracking devices in block 210. If the user does not alter or change the device at rest or add intra-operative imaging constraints, then a NO-path can be followed through block 394 to continue navigation in block 210. Thus, it is understood that the navigation system, to evaluate whether the flexible instrument 110b is at a possible or probable location, can use the flowchart 300 that can include features similar to that in the flowchart 200 but further includes separate evaluation of both simple and model constraints.

Example embodiments are provided so that this disclosure will be thorough, and will fully convey the scope to those who are skilled in the art. Numerous specific details are set forth such as examples of specific components, devices, and methods, to provide a thorough understanding of embodiments of the present disclosure. It will be apparent to those skilled in the art that specific details need not be employed, that example embodiments may be embodied in many different forms and that neither should be construed to limit the scope of the disclosure. In some example embodiments, well-known processes, well-known device structures, and well-known technologies are not described in detail.

The terminology used herein is for the purpose of describing particular example embodiments only and is not intended to be limiting. As used herein, the singular forms "a," "an," and "the" may be intended to include the plural forms as well, unless the context clearly indicates otherwise.

Terms such as "first," "second," and other numerical terms when used herein do not imply a sequence or order unless clearly indicated by the context. Thus, a first element, component, region, layer or section discussed below could be termed a second element, component, region, layer or section without departing from the teachings of the example embodiments.

The foregoing description of the embodiments has been provided for purposes of illustration and description. It is not intended to be exhaustive or to limit the disclosure. Individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the disclosure, and all such modifications are intended to be included within the scope of the disclosure.

What is claimed is:

1. A method to determine proper navigation of a flexible instrument in a navigation field, comprising:
    evaluating and predetermining physical constraints of the flexible instrument;
    predetermining a calibrated position that is a relaxed position of a first tracking device and a second tracking device both fixed to the flexible instrument;
    storing with a first memory portion the physical constraints of the flexible instrument;
    storing with a second memory portion the calibrated position of the first tracking device and the second tracking device that are both fixed to the flexible instrument; and
    operating a processor to recall the stored physical constraints and stored calibrated position;
    wherein the processor is able to be operated to execute an algorithm to determine an energy of bending of the flexible instrument based on the recalled stored physical constraints and accessed stored calibrated position and at least by evaluating curve parameters and curve tangents.

2. The method of claim 1, further comprising:
    operating the processor to:
        determine the energy of bending based on (i) a current tracked position of both the first tracking device and the second tracking device and (ii) the stored physical constraints, and (iii) the stored calibrated position of the first tracking device and the second tracking device; and
        based on the determined energy of bending, determine whether the determined energy of bending is probable based on the stored physical constraints and the stored calibrated position of the first tracking device and the second tracking device;
        selectively determining whether distortion is present in the navigation field based on the determined energy of bending.

3. The method of claim 2, further comprising:
    executing the algorithm with the processor to determine the energy of bending based on at least one of a distance between a tracked location of the first tracking device and the second tracking device or determining an estimated arc length of the flexible instrument between the first tracking device and the second tracking device.

4. The method of claim 3, wherein evaluating and predetermining physical constraints of the flexible instrument includes determining of the flexible instrument at least one of a wire constant, a modulus of elasticity, a dimension, or combinations thereof.

5. The method of claim 3, further comprising:
    operating the processor to determine whether the determined energy of bending is expected, unlikely, or forbidden.

6. The method of claim 5, further comprising:
    determining a probability value of the determined energy of bending based on whether a value of the determined energy of bending is greater than a threshold energy value.

7. The method of claim 3, further comprising:
    determining an intra-procedure physical constraint based at least on a physical feature of the subject and the evaluated and predetermined physical constraints;
    determining a maximum energy of bending based on the determined intra- procedure physical constraint; and
    comparing the maximum energy of bending to the determined energy of bending.

8. The method of claim 1, wherein evaluating physical constraints of a flexible instrument includes:
    predetermining a parameterized energy of the flexible instrument between the first tracking device and the second tracking device; and
    predetermining an energy functional based on the parameterized energy of the flexible instrument between the first tracking device and the second tracking device.

9. The method of claim 8, further comprising:
operating the processor to determine a minimization of the energy functional to determine a probable location and orientation of the flexible instrument.

10. The method of claim 1, further comprising:
determining that a distortion is present in a generated electromagnetic field if a probability value of the energy of bending based on the determined value of the energy of bending is greater than a threshold energy value;
wherein the threshold energy value and determined value of energy of bending are based on the evaluated and predetermined physical constraints.

11. The method of claim 10, further comprising:
generating the electromagnetic field; and
tracking the first tracking device and the second tracking device by sensing the generated electromagnetic field in a navigation space.

12. The method of claim 1, providing a single memory device as the first memory portion and the second memory portion.

13. An instrument system operable with a navigation system within a navigation field to determine proper navigation of the instrument in the navigation field, comprising:
a flexible instrument extending at least between a first portion and a second portion;
a first tracking device fixed to the flexible instrument at the first portion; and
a second tracking device fixed to the flexible instrument at the second portion;
wherein,
the first tracking device is configured to generate a first signal and transmit the first signal to the navigation system;
the second tracking device is configured to generate a second signal and transmit the second signal to the navigation system;
a predetermined parameterized energy between the first tracking device and the second tracking device is known regarding the flexible instrument and a predetermined energy functional based on the predetermined parameterized energy of the flexible instrument between the first tracking device and the second tracking device; and
a probable location and orientation of the instrument is operable to be a determined based on a minimization of the predetermined energy functional.

14. The system of claim 13, further comprising:
a memory system having stored thereon at least one instrument physical constraint based on a physical characteristic of the flexible instrument at least between a first instrument position and a second instrument position.

15. The system of claim 14, further comprising:
the navigation system having a processor configured to:
access the stored at least one instrument physical constraint stored on the memory system; and
execute an algorithm to determine an energy of bending of the flexible instrument based on the accessed stored at least one instrument physical constraint of the flexible instrument and the determined minimization of the predetermined energy functional.

16. The system of claim 15, wherein the processor is further configured to deem improper navigation due at least in part to distortion in a navigation field if a relative location and orientation of the first tracking device and the second tracking device is determined to be improbable based on the recalled at least one instrument physical constraint and the predetermined energy functional.

17. The system of claim 13, wherein the navigation of the instrument is able to be deemed improper by the navigation system if the relative location and orientation of the first tracking device and the second tracking device is determined to be improbable based on the recalled at least one instrument constraint.

18. The system of claim 13, wherein the instrument is able to flex to change at least one of a relative distance or orientation between the first portion and the second portion.

19. The system of claim 13, wherein the predetermined parameterized energy is operable to identify an energy threshold and forbidden energies of the instrument.

20. The system of claim 13, wherein the predetermined energy functional includes constraints for at least one instrument flexibility, instrument extensions, instrument twist, or instrument compression.

21. A system to determine proper navigation of a flexible instrument in a navigation field, comprising:
a localizer to generate an electromagnetic field as the navigation field;
a navigation processor configured for:
receiving a first signal from a first tracking device associated with the flexible instrument;
receiving a second signal from a second tracking device associated with the flexible instrument;
determining a relative position of the first tracking device and the second tracking device based on the respective received first signal and second signal; and
determining whether the determined relative position of the first tracking device and the second tracking device is probable based on (i) a predetermined physical parameterized energy of the flexible instrument between the first tracking device and the second tracking device, (ii) a predetermined energy functional based on the physical parameterized energy of the instrument between the first tracking device and the second tracking device, and (iii) an evaluation of the predetermined energy functional;
wherein the predetermined energy functional includes curve parameters and curve tangents and a calibrated arc length.

22. The system of claim 21, further comprising:
the flexible instrument configured to be moved relative to the navigation field;
the first tracking device fixed to the flexible instrument at a first position; and
the second tracking device fixed to the flexible instrument at a second position spaced apart from the first position.

23. The system of claim 21, further comprising:
a notification system configured to notify a user that the evaluation of the predetermined energy functional is at least one of expected, unlikely, or forbidden.

24. The system of claim 21, further comprising:
a display device configured to illustrate a model of the flexible instrument;
wherein the model of the flexible instrument is based on the determined relative position of the first tracking device and the second tracking device and the predetermined physical parameterizable energy.

25. The system of claim 21, wherein the navigation processor is further configured for determining whether the determined relative position of the first tracking device and the second tracking device is probable based on a minimization of the energy functional;

wherein the physical parameterizable energy includes at least one of an energy of bending, a torsion energy, a compression energy, extending energy, or a rotation energy.

* * * * *

UNITED STATES PATENT AND TRADEMARK OFFICE
CERTIFICATE OF CORRECTION

PATENT NO.            : 11,331,001 B2                                Page 1 of 1
APPLICATION NO.       : 15/664778
DATED                 : May 17, 2022
INVENTOR(S)           : Brad Jacobsen et al.

It is certified that error appears in the above-identified patent and that said Letters Patent is hereby corrected as shown below:

On the Title Page

NPL Documents, Page 2, Line 21, delete "Lenght," and insert --Length,-- therefor NPL Documents, Page 2, Line 28, delete "Countours" and insert --Contours-- therefor In the Specification Column 3, Line 16, after "animal", insert --.--

Column 5, Line 43, delete "28." and insert --26.-- therefor

Column 7, Line 29, delete "521," and insert --52l,-- therefor

Column 10, Line 4, delete "48," and insert --40,-- therefor

Column 12, Line 54, delete "110*a*" and insert --110*b*-- therefor

Column 13, Line 36, delete "100*b*." and insert --110*b*.-- therefor

Column 18, Line 25, delete "110*b*1" and insert --110bl-- therefor

Column 28, Line 13, delete "24" and insert --22-- therefor

Column 28, Line 54, delete "24" and insert --22-- therefor

Signed and Sealed this
Sixth Day of September, 2022

Katherine Kelly Vidal
*Director of the United States Patent and Trademark Office*